US011793769B2

(12) United States Patent
Knudsen

(10) Patent No.: US 11,793,769 B2
(45) Date of Patent: Oct. 24, 2023

(54) DEVICE WITH COMPOSITIONS FOR DELIVERY TO THE LUNGS, THE ORAL MUCOSA AND THE BRAIN

(71) Applicants: Jai Shankar Sukul, Brampton (CA); CLK Consult v/ Carsten Leonhard Knudsen CPR NO 020460-0457, Nexø (DK)

(72) Inventor: Carsten Leonhard Knudsen, Hørsholm (DK)

(73) Assignees: Jai Shankar Sukul, Brampton (CA); CLK Consult v/Carsten Leonhard Knudsen CPR NO 020460-0457, Nexø (DK)

( * ) Notice: Subject to any disclaimer, the term of this patent is extended or adjusted under 35 U.S.C. 154(b) by 0 days.

(21) Appl. No.: 15/506,630

(22) PCT Filed: Aug. 25, 2015

(86) PCT No.: PCT/EP2015/069439
§ 371 (c)(1),
(2) Date: Feb. 24, 2017

(87) PCT Pub. No.: WO2016/030369
PCT Pub. Date: Mar. 3, 2016

(65) Prior Publication Data
US 2017/0273914 A1 Sep. 28, 2017

(30) Foreign Application Priority Data

Aug. 25, 2014 (DK) .............................. PA201400473

(51) Int. Cl.
*A61K 31/65* (2006.01)
*A61K 31/167* (2006.01)
*A61K 31/192* (2006.01)
*A61K 31/05* (2006.01)
*A61K 36/81* (2006.01)
*A61K 31/352* (2006.01)
*A61K 36/185* (2006.01)
*A61M 11/04* (2006.01)
*A61M 15/06* (2006.01)
*A61M 15/08* (2006.01)
*A61K 45/06* (2006.01)
*A61K 36/534* (2006.01)
*A61K 31/522* (2006.01)
*A61K 31/4468* (2006.01)
*A24F 42/20* (2020.01)
*A61M 15/00* (2006.01)
*A61K 9/00* (2006.01)
*A61K 31/465* (2006.01)
*A61K 47/46* (2006.01)

(52) U.S. Cl.
CPC .............. *A61K 31/05* (2013.01); *A24F 42/20* (2020.01); *A61K 9/0073* (2013.01); *A61K 31/167* (2013.01); *A61K 31/192* (2013.01); *A61K 31/352* (2013.01); *A61K 31/4468* (2013.01); *A61K 31/465* (2013.01); *A61K 31/522* (2013.01); *A61K 36/185* (2013.01); *A61K 36/534* (2013.01); *A61K 36/81* (2013.01); *A61K 45/06* (2013.01); *A61K 47/46* (2013.01); *A61M 11/041* (2013.01); *A61M 15/0041* (2014.02); *A61M 15/06* (2013.01); *A61M 15/08* (2013.01); *A61K 2236/15* (2013.01); *A61K 2236/19* (2013.01); *A61K 2236/33* (2013.01); *A61M 2205/581* (2013.01); *A61M 2205/584* (2013.01); *A61M 2205/8206* (2013.01)

(58) Field of Classification Search
CPC ..... A24F 42/20; A61K 31/658; A61K 31/167; A61K 31/192
USPC ......................................... 514/456, 560, 593
See application file for complete search history.

(56) References Cited

U.S. PATENT DOCUMENTS

| 4,793,366 A * | 12/1988 | Hill ........................ A24F 42/60 131/273 |
| 2004/0118396 A1 | 6/2004 | Hughes et al. |
| 2005/0042172 A1 * | 2/2005 | Whittle ................ A61K 31/00 424/46 |
| 2005/0063686 A1 * | 3/2005 | Whittle |
| 2005/0123635 A1 * | 6/2005 | McAughey ............ A61K 9/007 424/774 |

(Continued)

FOREIGN PATENT DOCUMENTS

| GB | 2 412 876 A | 10/2005 |
| GB | 2 431 105 | 4/2007 |

(Continued)

OTHER PUBLICATIONS

Niedbala et al., "Passive Cannabis Smoke Exposure and Oral Fluid Testing. II. Two Studies of Extreme Cannabis Smoke Exposure in a Motor Vehicle", J.Anal. Tox., 2005, vol. 29, pp. 607-615 (Year: 2005).*

(Continued)

*Primary Examiner* — Raymond J Henley, III
(74) *Attorney, Agent, or Firm* — Morrison & Foerster LLP

(57) ABSTRACT

The present invention provides a passive inhaler for use in treating a number of diseases. The inventor has shown that the compositions comprised in the inhaler can be delivered to the lungs and to the brain in pharmacological relevant dosages, to treat a number of diseases in the lungs and the brain. Further, the inhaler is also able to deliver substances to the brain which may enhance transport across the blood brain barrier.

19 Claims, 2 Drawing Sheets

(56) References Cited

U.S. PATENT DOCUMENTS

| | | | | |
|---|---|---|---|---|
| 2009/0197941 | A1* | 8/2009 | Guy | A61K 31/05 514/454 |
| 2010/0012118 | A1* | 1/2010 | Storz | A61M 11/04 128/203.15 |
| 2010/0258118 | A1* | 10/2010 | Morton | A61K 9/0075 128/203.15 |
| 2011/0036346 | A1* | 2/2011 | Cohen | A24F 40/40 128/200.14 |
| 2011/0308521 | A1* | 12/2011 | Kofford | A61M 11/041 128/203.27 |
| 2012/0000478 | A1* | 1/2012 | Wagenhals | A24F 13/04 131/329 |
| 2012/0304990 | A1* | 12/2012 | Todd | A61M 11/042 128/203.14 |
| 2013/0087144 | A1* | 4/2013 | Todd | A61B 5/1171 128/203.14 |
| 2013/0276799 | A1* | 10/2013 | Davidson | A24F 47/004 131/273 |

FOREIGN PATENT DOCUMENTS

| | | |
|---|---|---|
| GB | 2 461 108 A | 12/2009 |
| WO | WO-01/66089 | 9/2001 |
| WO | WO2004/000290 A1 | 12/2002 |
| WO | WO-03/006010 | 1/2003 |
| WO | WO-2008/053253 | 5/2008 |
| WO | WO-2011/107104 | 9/2011 |
| WO | WO-2014/029400 | 2/2014 |
| WO | WO-2014/033439 | 3/2014 |
| WO | WO2015/073854 A2 | 5/2015 |

OTHER PUBLICATIONS

Chemical Abstracts Service Registry No. 1972-08-3, accessed May 4, 2018 (Year: 2018).*

International Search Report dated Jan. 11, 2016, directed to International Application No. PCT/EP2015/069439, 7 pages.

Almeida et al., "Borneol, A Bicyclic Monoterpene Alcohol, Reduces Nociceptive Behavior and Inflammatory Response in Mice", The Scientific World Journal, vol. 2013, Article ID 808460, 2013, pp. 1-5.

Archana et al., "Modulation of Gamma Ray-Induced Genotoxic Effect by Thymol, A Monoterpene Phenol Derivative of Cymene", Integrative Cancer Therapies, vol. 10, No. 4, 2011, pp. 374-383.

Arvanitidis et al., "Genetic Polymorphisms of Drug-Metabolizing Enzymes CYP2D6, CYP2C9, CYP2C19 and CYP3A5 in the Greek Population", Fundamental & Clinical Pharmacology, vol. 21, 2007, pp. 419-426.

Berliocchi et al., "(−)-Linalool Attenuates Allodynia in Neuropathic Pain Induced by Spinal Nerve Ligation in C57/BL6 Mice", International Review of Neurobiology, vol. 85, 2009, pp. 221-235.

Bounihi et al., "In Vivo Potential Anti-Inflammatory Activity of Melissa Officinalis L. Essential Oil", Advances in Pharmacological Sciences, vol. 2013, Article ID 101759, 2013, pp. 1-7.

Castro et al., "Aspirin and Indomethacin Reduce Lung Inflammation of Mice Exposed to Cigarette Smoke", Biochemical Pharmacology, vol. 77, 2009, pp. 1029-1039.

Cherng et al., "Chemopreventive Effects of Minor Dietary Constituents in Common Foods on Human Cancer Cells", Bioscience, Biotechnology, and Biochemistry, No. 71, No. 6, 2007, pp. 1500-1504.

Eagan et al., "Systemic Inflammatory Markers in COPD: Results from the Bergen COPD Cohort Study", The European Respiratory Journal, vol. 35, No. 3, 2010, pp. 540-548.

Ferreira et al., "Nerolidol Effects on Mitochondrial and Cellular Energetics", Toxicol in Vitro, vol. 26, 2012, pp. 189-196.

Fiorenzani et al., "In Vitro and In Vivo Characterization of the New Analgesic Combination Beta-Caryophyllene and Docosahexaenoic Acid", Evidence-Based Complementary and Alternative Medicine, vol. 2014, Article ID 596312, 2014, pp. 1-12.

Gui et al., "Oridonin Alters the Expression Profiles of MicroRNAs in BxPC-3 Human Pancreatic Cancer Cells", BMC Complementary and Alternative Medicine, vol. 15, No. 117, 2015, pp. 1-10.

Hanuš et al., "Enantiomeric Cannabidiol Derivatives: Synthesis and Binding to Cannabinoid Receptors", Organic & Biomolecular Chemistry, vol. 3, 2005, pp. 1116-1123.

Ikezoe et al., "Oridonin Induces Growth Inhibition and Apoptosis of a Variety of Human Cancer Cells", International Journal of Oncology, vol. 23, 2003, pp. 1187-1193.

International Preliminary Report on Patentability received for PCT Patent Application No. PCT/EP2015/069439, dated Mar. 9, 2017, 13 pages.

Jaggi et al., "Analgesic Potential of Intrathecal Famesyl Thiosalicylic Acid and GW 5074 in Vincristine-induced Neuropathic Pain in Rats", Food and Chemical Toxicology, vol. 50, 2012, pp. 1295-1301.

Jiang et al., "(+)-Borneol Alleviates Mechanical Hyperalgesia in Models of Chronic Inflammatory and Neuropathic Pain in Mice", European Journal of Pharmacology, vol. 757, 2015, pp. 53-58.

Juergens, U. R., "Anti-inflammatory Properties of the Monoterpene 1.8-Cineole: Current Evidence for Co-medication in Inflammatory Airway Diseases", Drug Research, vol. 64, 2014, pp. 638-646.

Khader et al., "Thymoquinone: An Emerging Natural Drug with a Wide Range of Medical Applications", Iranian Journal of Basic Medical Sciences, vol. 17, No. 12, 2014, pp. 950-957.

Klauke et al., "The Cannabinoid CB2 Receptor-Selective Phytocannabinoid Beta-Caryophyllene Exerts Analgesic effects in Mouse Models of Inflammatory and Neuropathic Pain", European Neuropsychopharmacology, vol. 24, 2014, pp. 608-620.

Kuwahata et al., "Peripherally Injected Linalool and Bergamot Essential Oil Attenuate Mechanical Allodynia via Inhibiting Spinal ERK Phosphorylation", Pharmacology, Biochemistry and Behavior, vol. 103, 2013, pp. 735-741.

Murata et al., "Antitumor Effect of 1, 8-Cineole against Colon Cancer", Oncology Reports, vol. 30, 2013, pp. 2647-2652.

Ninomiya et al., "Suppression of Inflammatory Reactions by Terpinen-4-ol, A Main Constituent of Tea Tree Oil, in a Murine Model of Oral Candidiasis and its Suppressive Activity to Cytokine Production of Macrophages in Vitro", Biol. Pharm. Bull., vol. 36, No. 5, 2013, pp. 838-844.

Nishijima et al., "Citral: A Monoterpene with Prophylactic and Therapeutic Anti-Nociceptive Effects in Experimental Models of Acute and Chronic Pain", European Journal of Pharmacology, vol. 736, 2014, pp. 16-25.

Peana et al., "Anti-Inflammatory Activity of Linalool and Linalyl Acetate Constituents of Essential Oils", Phytomedicine, vol. 9, 2002, pp. 721-726.

Pejin et al., "An Insight into the Cytotoxic Activity of Phytol at in Vitro Conditions", Natural Product Research, vol. 28, No. 22, 2014, pp. 2053-2056.

Quintão et al., "Chemical Composition and Evaluation of the Anti-Hypernociceptive Effect of the Essential Oil Extracted from the Leaves of Ugni Myricoides on Inflammatory and Neuropathic Models of Pain in Mice", Planta Medica, vol. 76, 2010, pp. 1411-1418.

Raskovic et al., "Analgesic Effects of Rosemary Essential Oil and its Interactions with Codeine and Paracetamol in Mice", European Review for Medical and Pharmacological Sciences, vol. 19, 2015, pp. 165-172.

Rog et al., "Oromucosal $\Delta^9$-Tetrahydrocannabinol/Cannabidiol for Neuropathic Pain Associated with Multiple Sclerosis: An Uncontrolled, Open-Label, 2-Year Extension Trial", Clinical Therapeutics, vol. 29, No. 9, 2007, pp. 2068-2079.

Russo, Ethan B., "Taming THC: Potential Cannabis Synergy and Phytocannabinoid-Terpenoid Entourage Effects", British Journal of Pharmacology, vol. 163, 2011, pp. 1344-1364.

Sakurada et al., "Intraplantar Injection of Bergamot Essential Oil Induces Peripheral Antinociception Mediated by Opioid Mechanism", Pharmacology, Biochemistry and Behavior, vol. 97, 2011, pp. 436-443.

Selim et al., "Chemical Composition, Antimicrobial and Antibiofilm Activity of the Essential Oil and Methanol Extract of the Mediter-

(56) References Cited

OTHER PUBLICATIONS ranean Cypress (*Cupressus sempervirens* L.)", BMC Complementary and Alternative Medicine, vol. 14, No. 179, 2014, pp. 1-8.
Sobral et al., "Antitumor Activity of Monoterpenes Found in Essential Oils", The Scientific World Journal, vol. 2014, Article ID 953451, 2014, pp. 1-35.
Stotz et al., "Citral Sensing by TRANSient Receptor Potential Channels in Dorsal Root Ganglion Neurons", Plos One, vol. 3, No. 5, May 2008, pp. 1-14.
Tsou et al., "Lead Screening for Chronic Obstructive Pulmonary Disease of IKK2 Inhibited by Traditional Chinese Medicine", Evidence-Based Complementary and Alternative Medicine, vol. 2014, Article ID 465025, 2014, pp. 1-16.
Ulasli et al., "Anticancer Effects of Thymoquinone, Caffeic Acid Phenethyl Ester and Resveratrol on A549 Non-small Cell Lung Cancer Cells Exposed to Benzo(a)pyrene", Asian Pacific Journal of Cancer Prevention, vol. 14, 2013, pp. 6159-6164.
Ward et al., "Cannabidiol Inhibits Paclitaxel-induced Neuropathic Pain through 5-HTIA Receptors without Diminishing Nervous System Function or Chemotherapy Efficacy", British Journal of Pharmacology, vol. 171, 2014, pp. 636-645.
Written Opinion received for PCT Patent Application No. PCT/EP2015/069439, dated Jan. 11, 2016, 11 pages.
Wu et al., "Linalool Attenuates Lung Inflammation induced by Pasteurella Multocida via Activating Nrf-2 Signaling Pathway", International Immunopharmacology, vol. 21, 2014, pp. 456-463.
Wu et al., "γ-Terplneol Inhibits Cell Growth and induces Apoptosis in Human Liver Cancer BEL-7402 Cells in Vitro", Int. J. Clin. Exp. Pathol., vol. 7, No. 10, 2014, pp. 6524-6533.
Zhou et al., "Thymol Attenuates Allergic Airway Inflammation in Ovalbumin (OVA)-induced Mouse Asthma", Fitoterapia, vol. 96, 2014, pp. 131-137.
"Nicotine Inhaler: The Great Imitator", The University of Texas M.D Anderson Cancer Center (retrieved Mar. 23, 2021), Published on Dec. 17, 2004 as per Wayback Machine.
"Spray Nozzle", Wikipedia, retrieved Mar. 22, 2022.

\* cited by examiner

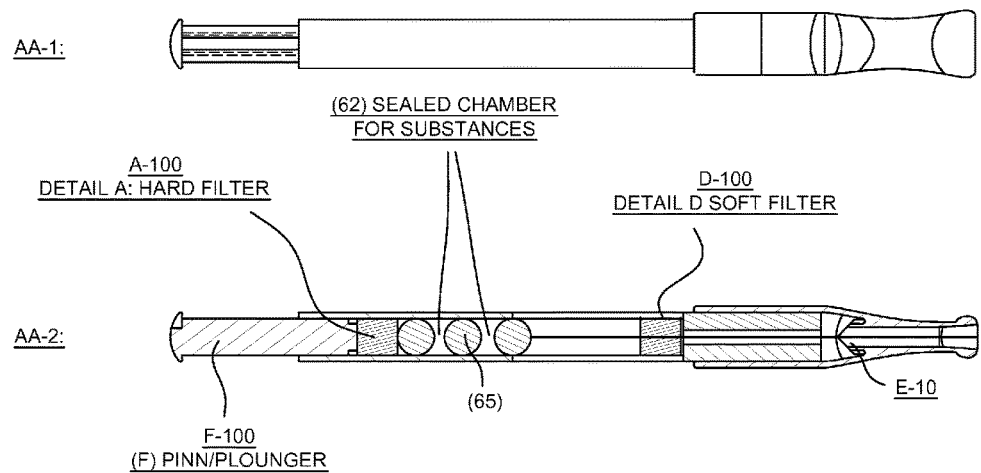
FIGURE 1. VAVE DEVICE WITH MOUTH PIECE
(NO CAP TUBE)
(II) FILTER IMPROVED INHALER

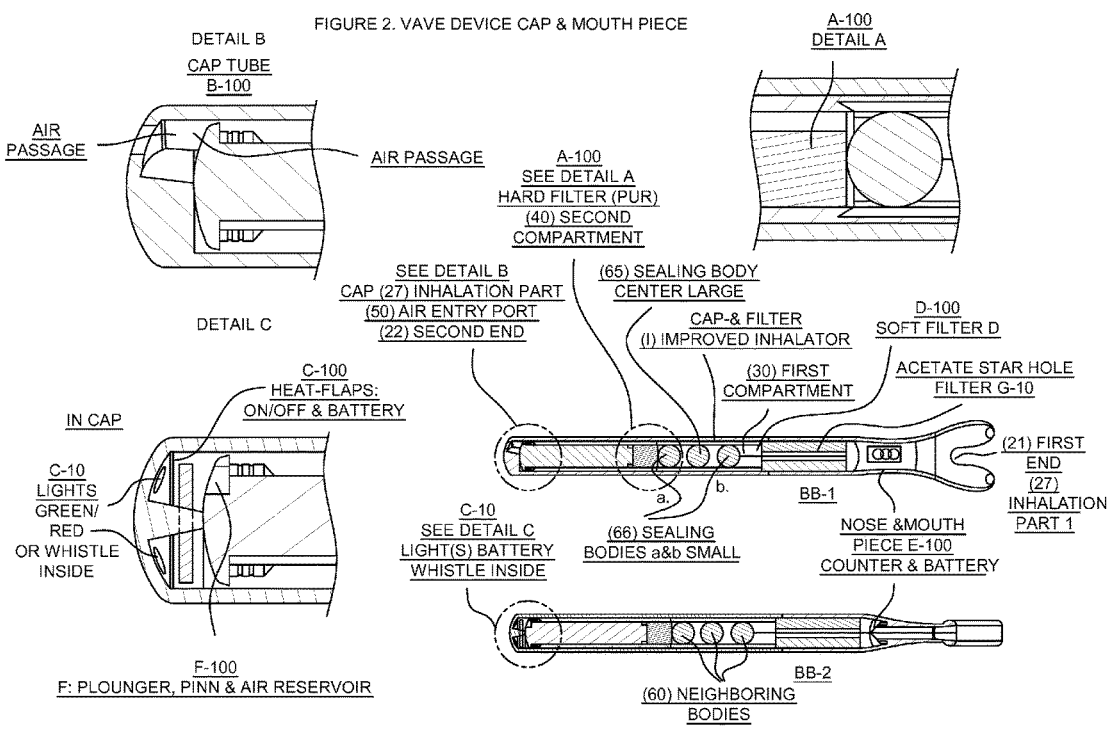

DEVICE WITH COMPOSITIONS FOR DELIVERY TO THE LUNGS, THE ORAL MUCOSA AND THE BRAIN

CROSS-REFERENCE TO RELATED APPLICATIONS

This application is a U.S. National Phase patent application of International Patent Application No. PCT/EP2015/069439, filed Aug. 25, 2015, which claims priority to Danish Application No. PA201400473, filed Aug. 25, 2014, each of which is hereby incorporated by reference in the present disclosure in its entirety.

FIELD OF THE INVENTION

The present invention provides a passive inhaler comprising compositions which comprises cannabidiol or a derivative or a variant thereof. Further, the device comprises a carrier. The device is suitable for delivery of CBD as a vapor to the oral cavity and to the lungs. It is a characteristic of the device that it is able to deliver sufficient amounts of CBD to the oral cavity, for it to be delivered to the brain in a quantity which is relevant in order to accomplish a pharmacologic effect of the CBD in the brain. The passive inhaler device is able to deliver CBD to the brain for use in various applications. In some instances, the inhaler comprises cannabidiol or a derivative or a variant thereof, or THC or a derivative thereof or a terpene or a combination of any one of those, for delivery as a gas, or a vapor or an aerosol or a mist into the oral cavity for uptake and transport to the brain, for the treatment, prevention or alleviationment of various conditions, such as pain, anxiety, depression or plaque related diseases. In some instances, the inhaler comprises flavours, which may in some embodiments be in the form of terpenes, for delivery to the brain for enhancing transport of other substances such as in example nutrients or active pharmaceutical ingredients (API) across the blood brain barrier.

BACKGROUND OF THE INVENTION

There is a need for novel or improved treatments for a number of brain diseases, and additionally a need for enhancement of delivery of otherwise effective API across the blood brain barrier in order to facilitate the action of such API on their brain targets, by making the API available to have effect on the target on site in the brain. The present invention provides means to improve treatment of such diseases, and to enhance delivery locally to the brain of API which are present in the blood circulation but unable to pass the blood brain barrier in sufficient amount.

Pain

Pain in various forms and origin affects the lives of many people every day. Several types of pain exist, including neuropathic pain, nociceptive pain and psychogenic pain.

Neuropathic Pain

Neuropathic pain is caused by damage to or dysfunction of the nerves, spinal cord, or brain.

Neuropathic pain may be felt as burning or tingling or as hypersensitivity to touch or cold. Causes include compression of a nerve (for example, by a tumor, by a ruptured intervertebral disk, or as occurs in carpal tunnel syndrome), nerve damage (for example, as occurs in a metabolic disorder such as diabetes mellitus), and abnormal or disrupted processing of pain signals by the brain and spinal cord. Processing of pain is abnormal in phantom limb pain, postherpetic neuralgia, and complex regional pain syndrome.

Phantom Limb Pain

Pain seems to be felt in an amputated part of the body, usually a limb. It differs from phantom limb sensation—the feeling that the amputated part is still there—which is much more common. Phantom limb pain cannot be caused by a problem in the limb. Rather, it must be caused by a change in the nervous system above the site where the limb was amputated. But the brain misinterprets the nerve signals as coming from the amputated limb. Usually, the pain seems to be in the toes, ankle, and foot of an amputated leg or in the fingers and hand of an amputated arm. The pain may resemble squeezing, burning, or crushing sensations, but it often differs from any sensation previously experienced. For some people, phantom limb pain occurs less frequently as time passes, but for others, it persists. Massage can sometimes help, but drug therapy is sometimes necessary.

Postherpetic Neuralgia

This disorder results from herpes zoster (shingles, which causes inflammation of nerve tissue), but occurs only after shingles resolves (see Postherpetic Neuralgia). What causes postherpetic neuralgia is unknown. The pain is felt as a constant deep aching or burning, as a sharp and intermittent pain, or as hypersensitivity to touch or cold. The pain may be debilitating. Pain relievers and other drugs may be required, but no treatment is routinely effective.

Complex Regional Pain Syndrome

This chronic pain syndrome is defined as persistent burning pain accompanied by certain abnormalities that occur in the same area as the pain. Abnormalities include increased or decreased sweating, swelling, changes in skin color, damage to the skin, hair loss, cracked or thickened nails, muscle wasting and weakness, and bone loss. This syndrome typically occurs after an injury. There are two types:

Type 1, which used to be called reflex sympathetic dystrophy, results from injury to tissues other than nerve tissue, as when bone is crushed in an accident or when heart tissue is damaged in a heart attack.

Type 2, which used to be called causalgia, results from injury to nerve tissue. Sometimes complex regional pain syndrome is made worse by activity of the sympathetic nervous system, which normally prepares the body for stressful or emergency situations—for fight or flight. For this reason, doctors may suggest treatment with a sympathetic nerve block (see Pain:Anesthetics). Physical therapy and drugs may also help.

Nociceptive Pain

Nociceptive pain is caused by an injury to body tissues.

The injury may be a cut, bruise, bone fracture, crush injury, burn, or anything that damages tissues. This type of pain is typically aching, sharp, or throbbing. Most pain is nociceptive pain. Pain receptors for tissue injury (nociceptors) are located mostly in the skin or in internal organs.

The pain almost universally experienced after surgery is nociceptive pain. The pain may be constant or intermittent, often worsening when a person moves, coughs, laughs, or breathes deeply or when the dressings over the surgical wound are changed.

Most of the pain due to cancer is nociceptive. When a tumor invades bones and organs, it may cause mild discomfort or severe, unrelenting pain. Some cancer treatments, such as surgery and radiation therapy, can also cause nociceptive pain. Pain relievers (analgesics), including opioids, are usually effective.

Psychogenic Pain

Psychogenic pain is pain that is mostly related to psychologic factors.

When people have persistent pain with evidence of psychologic disturbances and without evidence of a disorder that could account for the pain or its severity, the pain may be described as psychogenic. However, psychophysiologic pain is a more accurate term because the pain results from interaction of physical and psychologic factors. Psychogenic pain is far less common than nociceptive or neuropathic pain.

Any kind of pain can be complicated by psychologic factors. Psychologic factors often contribute to chronic pain and may contribute to pain-related disability. In such cases, the pain, disability, or both usually have a physical cause, but psychologic factors exaggerate or enhance the pain, making it worse than what most people with a similar physical disorder experience. For example, people with chronic pain know it will recur and may become fearful and anxious as they anticipate the pain. These emotions make them more sensitive to pain. Sometimes doctors describe chronic pain that is worsened by psychologic factors as a chronic pain syndrome.

The fact that pain is caused or worsened by psychologic factors does not mean that it is not real. Most people who report pain are really experiencing it, even if a physical cause cannot be identified. Doctors always investigate whether a physical disorder is contributing to pain.

Pain complicated by psychologic factors requires treatment, often by a team that includes a psychologist or psychiatrist. Treatment for this type of pain varies from person to person, and doctors try to match the treatment with the person's needs. For most people who have chronic psychogenic pain, the goals of treatment are to improve comfort and physical and psychologic function. Doctors may make specific recommendations for gradually increasing physical and social activities. Drugs and nondrug treatments—such as biofeedback, relaxation training, distraction techniques, hypnosis, transcutaneous electrical nerve stimulation (TENS), and physical therapy—may be used. Psychologic counseling is often needed.

The present invention also provides treatments for alleviation of Complex Regional Pain Syndrome (CRPS), which is a disease of unknown cause, but which exhibit severe pain to touch, swelling of e.g. legs or arms, skin and or hair and or nail changes temperature changes in affected part of the body, muscle weakness, tremors and dystonia.

Present Treatment Modalities for Pain

There is a need for improved treatment modalities for different kinds of pain. Fast onset of action is important, but also treatments capable of adding to effects of existing treatments. Further, safety and tolerability is important. In example, cannabidiol is presently in some countries used to treat pain in patients suffering from multiple sclerosis. However, although cannabidiol (CBD) has some effect on such patients when administered orally in capsules, or by other means which make it systemically available, it is not sufficient to fully alleviate the pain. Furthermore, some patients do not respond to CBD when administered systemically or orally by ingestion of CBD in capsules. The present invention provides a means for delivering CBD to have improved speed of action, and also to add on the effect of systemically administered CBD, and further to treat pain in CBD non-responders (when administered systemically (orally or by other means which make it available in the blood circulation)).

The administration of CBD according to the present invention, may be in combination with existing treatments for pain, which is claimed.

Present Treatment of Anxiety and Depression

There is a need for improved treatment modalities for anxiety and depression, both speed of action, less side effects and more efficient effects on the diseases. De Mello Schier et al. (CNS Neurol Disord Drug Targets, 2014; 13(6): 953-60) describe in a review that CBD has been tested in animal models of anxiety and depression and exhibited both anti-anxiety and antidepressant effects.

The present invention provides an improved method for delivering CBD to the brain in small but pharmacologically relevant dosages. The CBD is delivered fast by inhalation, to provide a fast action, and in small dosages to reduce side effects, but is still effective on brain targets.

Treatment of Epilepsy

There is a need for further medications for treatment of epilepsy, as present treatments can control seizures in about 70% of patients. Furthermore, side effects are common for most epilepsy drugs on the market presently. Therefore, there is a need for improved methods for treating epilepsy.

Treatment of Motion Sickness

Motion sickness or kinetosis, or other causes for vomiting, has a need for improved medicines which are convenient for the patient to administer at any time or location. In example, swallowing a pill may be inconvenient, whereas inhaling a substance may be done without a neet to have water available. Therefore, the present invention provides a more convenient and safe anti-emetic drug for use in treating or preventing vomiting and the feeling of motion sickness. Further, safe, effective and convenient methods of treating side effects of opioid analgesics, side effects of general anaesthetics, side effects of chemotherapy, severe cases of gastroenteritis and morning sickness are also needed.

Treatment of COPD

Chronic obstructive pulmonary disease (COPD) is the name for a collection of lung diseases including chronic bronchitis, emphysema and chronic obstructive airways disease.

People with COPD have difficulties breathing, primarily due to the narrowing of their airways, this is called airflow obstruction.

Symptoms of COPD

Symptoms of chronic obstructive pulmonary disease (COPD) usually develop over a number of years, so you may not be aware you have the condition. COPD does not usually become noticeable until after the age of 35 and most people diagnosed with the condition are over 50 years old.

Symptoms include:

increasing breathlessness when exercising or moving around a persistent cough with phlegm that never seems to go away frequent chest infections, particularly in winter wheezing Middle-aged smokers and ex-smokers who have a persistent chesty cough (especially in the morning), breathlessness on slight exertion or persistent coughs and colds in the winter should see their GP or practice nurse for a simple breathing test.

If you have COPD, the airways of the lungs become inflamed and narrowed. As the air sacs get permanently damaged, it will become increasingly difficult to breathe out.

It is thought there are more than 3 million people living with the disease in the UK, of which only about 900,000 have been diagnosed. This is because many people who develop symptoms of COPD do not get medical help because they often dismiss their symptoms as a 'smoker's cough'.

COPD affects more men than women, although rates in women are increasing.

Present Treatment Modalities for COPD

Although the damage that has already occurred to your lungs cannot be reversed, you can slow down the progression of the disease. Stopping smoking is particularly effective at doing this.

Treatments for COPD usually involve relieving the symptoms with medication, for example by using an inhaler to make breathing easier. Pulmonary rehabilitation may also help increase the amount of exercise you are capable of doing.

Surgery is only an option for a small number of people with COPD.

While there is currently no cure for COPD, the sooner the condition is diagnosed and appropriate treatment begins, the less chance there is of severe lung damage.

Symptoms of COPD are often worse in winter, and it is common to have two or more flare-ups a year. A flare-up (also known as an exacerbation) is when your symptoms are particularly bad. This is one of the most common reasons for people being admitted to hospital in the UK.

Other signs of COPD can include: weight loss, tiredness and fatigue and swollen ankles.

Causes of COPD:

Smoking is the main cause of COPD and is thought to be responsible for around 90% of cases. The lining of the airways becomes inflamed and permanently damaged by smoking and this damage cannot be reversed.

Up to 25% of smokers develop COPD.

Exposure to other people's smoke increases the risk of COPD.

Exposure to certain types of dust and chemicals at work, including grains, isocyanates, cadmium and coal, has been linked to the development of COPD, even in people who do not smoke.

The risk of COPD is even higher if you breathe in dust or fumes in the workplace and you smoke.

According to some research, air pollution may be an additional risk factor for COPD.

However, at the moment it is not conclusive and research is continuing.

Present Treatment of COPD

There is no cure for COPD at present. Avoidance of exposure to the most important causes of COPD is presently the most effective treatment. Furthermore, certain medicines such as bronchodilators and also corticosteroids are used, depending on the severeness of the disease.

Lung Cancer

There are two major types of lung cancer, non-small cell lung cancer (NSCLC) and small cell lung cancer (SCLC). Staging lung cancer is based on whether the cancer is local or has spread from the lungs to the lymph nodes or other organs. Nonsmall cell lung cancer which accounts for about 85% of lung cancers is divided into three types of tumors: adenocarcinoma, squamous cell carcinoma and large cell carcinomas. Nonsmall cell lung cancer is staged in four stages depending on the degree of spreading:

Stages of Non-Small Cell Lung Cancer

Stage I: The cancer is located only in the lungs and has not spread to any lymph nodes.

Stage II: The cancer is in the lung and nearby lymph nodes.

Stage III: Cancer is found in the lung and in the lymph nodes in the middle of the chest, also described as locally advanced disease. Stage III has two subtypes:

If the cancer has spread only to lymph nodes on the same side of the chest where the cancer started, it is called stage IIIA.

If the cancer has spread to the lymph nodes on the opposite side of the chest, or above the collar bone, it is called stage IIIB.

Stage IV: This is the most advanced stage of lung cancer, and is also described as advanced disease. This is when the cancer has spread to both lungs, to fluid in the area around the lungs, or to another part of the body, such as the liver or other organs.

Small cell lung cancer accounts for 15% of lung cancers in the US, it is staged in two stages:

Limited stage where the cancer is found only on one side of the chest involving only one part of the lung and nearby lymph nodes.

Extensive stage, where the cancer has spread to other regions of the body. There is a need for improved treatments of lung cancer and of inflammatory diseases of the lungs.

Neurodegenerative Diseases.

Diseases in the CNS pose an increasing problem in the world today, as the ageing populations suffer increasing age related health problems. In particular, the number of patients with neurodegenerative diseases is increasing. Today, 5 million Americans suffer from Alzheimer's disease; 1 million from Parkinson's; 400,000 from multiple sclerosis (MS); 30,000 from amyotrophic lateral sclerosis (ALS or Lou Gehrig's disease), and 30,000 from Huntington's disease. Because neurodegenerative diseases strike primarily in mid- to late-life, the incidence is expected to soar as the population ages. (By 2030, as many as 1 in 5 Americans will be over the age of 65.) If left unchecked 30 years from now, more than 12 million Americans will suffer from neurodegenerative diseases. Finding treatments and cures for neurodegenerative diseases is a goal of increasing urgency.

Treating diseases in the CNS, not only requires good medicaments capable of imposing their effect on a disease target, they also need to be able to reach the target in the CNS, which is a great challenge due to the presence of the blood brain barrier which is impermeable to many drugs. There is therefore a great need for means and methods which increase the transport of medicaments or compositions to regions of the brain in need thereof.

More than 20 serious human diseases are characterized in that abnormal accumulation of amyloid fibrils in organs may lead to amyloidosis, and this may indeed play a role in various neurodegenerative disorders. Amyloids are insoluble fibrous protein aggregates sharing specific structural traits. They arise from at least 18 inappropriately folded versions of proteins and polypeptides present naturally in the body. These misfolded structures alter their proper configuration such that they erroneously interact with one another or other cell components forming insoluble fibrils.

Diseases Featuring Amyloid Plaques:

Disease Protein featured in parentheses, Alzheimer's disease (Beta amyloid, Aβ), Diabetes mellitus type 2, (IAPP (Amylin), AIAPP), Parkinson's disease (Alpha-synuclein), Transmissible spongiform encephalopathy e.g. Bovine spongiform encephalopathy (PrPSc, AprP), Fatal Familial Insomnia (PrPSc AprP), Huntington's Disease (Huntingtin), Medullary carcinoma of the thyroid (Calcitonin, Aca1), Cardiac arrhythmias, Isolated atrial amyloidosis (Atrial natriuretic factor, AANF), Atherosclerosis (Apolipoprotein AI, AApoA1), Rheumatoid arthritis (Serum amyloid A, Aortic medial amyloid, Medin, Amed), Prolactinomas (Prolactin, Apro), Familial amyloid polyneuropathy (Transthyretin, ATTR), Hereditary non-neuropathic systemic amyloidosis (Lysozym Alys), Dialysis related amyloidosisCX (Beta 2 microglobulin, Aβ2M), Finnish amyloidosis (Gelsolin, Age1), Lattice conical dystrophy (Keratoepithelin, Aker), Cerebral amyloid angiopathy (Beta amyloid, Aβ), Cerebral amyloid angiopathy (Icelandic type) (Cystatin, Acys), systemic AL amyloidosis, (Immunoglobulin light chain AL, AL), Sporadic Inclusion Body Myositis (S-IBM)

The International Society of Amyloidosis classifies amyloid fibrils based upon associated proteins.[17]

Tau deposits, along with beta-amyloid plaques, are among the characteristic features of Alzheimer's disease. These protein deposits disrupt the communication of the nerve cells in the brain and contribute to their degeneration. Despite intensive research there is no drug available to date which can prevent this detrimental process.

Delivery of Drugs Across the Blood Brain Barrier, or Export from the Brain of Unwanted Substances Such as Tau Deposits, or Beta-Amyloid:

Transport of substances across the blood brain barrier (BBB) is a restricted process, in order to keep the right balance of nutrients and other substances in the brain environment.

The restricted access of substances to the brain is a problem for access of certain drugs to their targets in the brain.

Furthermore, harmful substances such as TAU and amyloid—beta may in some disease states have difficulty in exiting the brain, and thereby cause damage to neurons. Cannabidiol (CBD) has been shown to not only have anti-inflammatory effects, but also to aid in transport across the blood brain barrier of beta amyloid (Bachmeier et al. 2013, Molecular and Cellular Neuroscience vol. 56, p 255-62).

Moreover, certain processes, such as changes in the level of metabolism in a certain area of the brain may influence transport across the BBB locally.

The present invention provides means for increasing local transport rates across the BBB, whereby drugs may enter the brain at a higher rate, and harmful substances may exit the brain at a higher rate than normal.

Cannabidiol and Other Plant Derived Compounds Such as Terpenes for Treatment of Pain.

Plant materials from the *Cannabis* family are known to comprise a large number of compounds which have been linked to have beneficial effects on different pain states, as well as on various cancers, including lung cancer and cancer in the CNS, and to a number of neurological and psychiatric conditions. Two of the most significant known chemical structures present in *Cannabis sativa* are delta-9-tetrahydrocannabinol (THC) and cannabidiol (CBD) (FIG. 1). FIG. 1A shows the structure of THC, and FIG. 1B shows the structure of CBD.

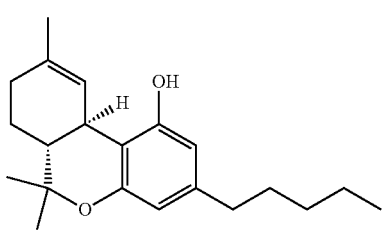

A

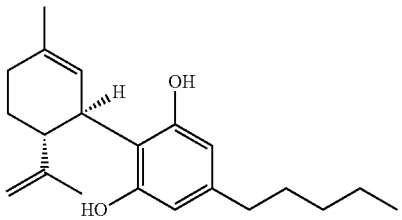

B

In contrary to THC, CBD is not a psychoactive molecule. However, CBD does possess a number of interesting and useful activities on the central nervous system and on the immune system, which may be useful therapeutically. Cannabidiol (CBD) pharmacologic effects are mediated by binding to two types of G-protein coupled receptors, cannabinoid type I and type II receptors (CB1 and CB2). CB1 is predominantly expressed in the central nervous system, and only shows very low affinity to CBD, whereas CBD has a higher affinity to the CB2 receptor which is primarily expressed in the immune system the spleen and the gastro-intestinal system, but to some extent also in the brain and peripheral nervous system.

There are investigations ongoing which examine the potential of CBD for treatment of neuropathic pain, Ward et al. (Br.J. Pharmacol 2014, February; 171(3); 636-645) showed that cannabidiol inhibits paclitaxel-induced neuropathic pain, without affecting the efficacy of the chemotherapy. Other variants such as CBC (Cannabichromene), CBD (Cannabidiol), CBGA (Cannabigerolic Acid), and CBN (Cannabinol) have also shown promise as analgesics.

A mix of a Delta(9)-Tetrahydrocannabinol/cannabidiol (THC/CBD) mix (27 mg/mL: 25 mg/mL) was tested in patients suffering from multiple sclerosis having central neuropathic pain (CNP). The CBD/THC mixture was delivered as an oral spray. Common side effects observed included dizziness and nausea (Roq et al. Clin.Ther. 2007 sep; 29(9): 2068-2079). Other variants of THC has shown promise as analgesic compounds, including Δ8-THC (Δ8-Tetrahydrocannabinol), Δ9-THC (Δ9-Tetrahydrocannabinol) and AEA (Anandamide).

Furthermore, Terpenes and terpenoids which may be derived from *cannabis* or from other plants, have shown promise for treatment of different pain states.

However, there is a need for improved compositions for treatment of these diseases, as well as convenient and effective methods for their delivery to the brain, for efficient and convenient treatment. The present invention provides such improved compositions, and means for their fast delivery to the brain for improved or for ad on to existing treatment.

The compositions may be used alone, of in combination with other treatments, such as systemic treatment with the compositions, or with other pain relieving medications.

SUMMARY OF THE INVENTION

The present invention provides a device comprising cannabidiol or a variant or a derivative thereof. In some embodiments the invention provides a device comprising a flavour. In some embodiments, the device further comprises a carrier. In some embodiments, the carrier is an essential oil, or a terpene, such as a mono-, di-, or a tri-terpene. In some embodiments, the carrier is a total terpene extract from a plant, such as in non-limiting example from *cannabis*. The device is designed for delivering the CBD and/or flavours to the brain via inhalation by puffing on the devicer to inhale the vapor from the device, and subsequent uptake from the oral mucosa or the lungs. Definition of puff is that the mouth is used to drag air through a passive inhaler to fill the mouth with air from the device. The air from the device is then included in the air that is breathed normally into the lungs. By including a puff in each breath (or in nearly each breath) over a prolonged period of time, the concentration of active ingredients in the lungs is built up, even in parts of the lungs which are not emptied or reached by the inhaled air. In the present invention, it is not essential that the air from the passive inhaler is taken into the lungs, as delivery to the brain preferably is by uptake through the mucosa of the oral cavity for transport to the brain.

Cannabidiol, Derivatives and Variants Thereof

Cannabidiol, its functional derivatives or variants, as well as the effects of any one of those on cannabinoid receptors are well described in the literature. Hanus et al. describes enantiomeric cannabidiol derivatives, their synthesis and binding to cannabinoid receptors (Hanus et al. Org Biomol Chem. 2005 Mar. 21; 3(6):1116-23).

Other derivatives, variants of CBD which bind to the CD2 receptor are well known in the art, and it will be of no burden to the skilled artisan to recognize such compounds.

THC has also been reported to have effects against pain, especially the THC derivative THCV (tetrahydrocannabivarin) has been shown to have effects and also potentially may have synergistic effects with e.g. CBD or terpenes in pain management (Russo 2011, British Journal of Pharmacology, 163, p 1344-1364).

In one embodiment, one or more of delta-9-THC, delta-8-THC, THCV, and cannabinol may be comprised in the compositions of the present invention. In one embodiment, THCV is comprised in the compositions of the invention. In one embodiment, delta-9-THC is comprised in the compositions of the present invention. In one embodiment, delta-8-THC is comprised in the compositions of the present invention. In one embodiment, cannabinol is comprised in the compositions of the present invention. In one embodiment, such compositions comprising one or more of THCV, delta-9-THC, delta-8-THC, and cannabinol are for use in treatment, prevention or alleviation of Pain, cancer, inflammatory diseases, neurological or psychiatric diseases. In one embodiment, the composition comprises one or more of THCV, delta-9-THC, delta-8-THC, and cannabinol and wherein the composition further comprises CBD. In one embodiment, the composition comprises CBD or a variant or derivative thereof and one or more of THCV, delta-9-THC, delta-8-THC, and cannabinol in a weight:weight (W:W) relationship of any one of a 1:1 w/w ratio, such as in a 1:2 ratio, such as in a 1:3 ratio, such as in a 1:4 ratio, such as in a 1:5 ratio, such as in a 1:6 ratio, such as in a 1:7 ratio, such as in a 1:8 ratio, such as in a 1:9 ratio, such as in a 1:10 ratio. In one embodiment, the composition comprises THCV or delta-9-THC and CBD in a W:W relationship THC:CBD in a 1:1 w/w ratio, such as in a 1:2 ratio, such as in a 1:3 ratio, such as in a 1:4 ratio, such as in a 1:5 ratio, such as in a 1:6 ratio, such as in a 1:7 ratio, such as in a 1:8 ratio, such as in a 1:9 ratio, such as in a 1:10 ratio. In one embodiment, the composition comprises delta-8-THC and CBD in a W:W relationship THC:CBD in a 1:1 w/w ratio, such as in a 1:2 ratio, such as in a 1:3 ratio, such as in a 1:4 ratio, such as in a 1:5 ratio, such as in a 1:6 ratio, such as in a 1:7 ratio, such as in a 1:8 ratio, such as in a 1:9 ratio, such as in a 1:10 ratio.

Terpenes and Terpenoids

Terpenes and terpenoids constitute an interesting class of compounds with great potential in medicine (Fischedick, J. T., 2013, Doctoral thesis, Leiden University). Terpenes are naturally occurring substances that are produced by a wide variety of plants and animals and may be used in the present invention. Terpenes are any of various isomeric hydrocarbons of formula C10H16 found present in essential oils (as from conifers) and used especially as solvents and in organic synthesis; in a broader definition, terpenes are any of numerous hydrocarbons (C5H8)n found especially in essential oils, resins, and balsams. A broad range of the biological properties of terpenoids have been described, which includes cancer chemopreventive effects and anti-inflammatory activities. Terpenes are also presented as skin penetration enhancers and agents involved in the prevention and therapy of several inflammatory diseases.

Terpenoids are defined as terpenes which contain additional functional groups.

In example, one important terpene which may be used in the present invention is 1.8-cineole which is a natural monoterpene, and which is also known as eucalyptol. It is a major compound of many plant essential oils, mainly extracted from *Eucalyptus globulus* oil. As an isolated compound, 1.8-cineole is known for its mucolytic and spasmolytic action on the respiratory tract, with proven clinical efficacy. 1.8-cineole has also shown therapeutic benefits in inflammatory airway diseases, such as asthma and chronic obstructive pulmonary disease (COPD) (Drug Res (Stuttg). 2014 December; 64(12):638-46, Juergens U R). Further, 1.8-cineole has been shown to induce apoptosis in certain cancer cells (Murata et al. Oncol Rep. 2013 December; 30(6):2647-52).

A whole set of terpenes known as *cannabis* terpenoids are terpenes which occur naturally in *cannabis*, but some are also found in other plants. Such terpenes are included in the present invention, and may as such be comprised in the compositions presented herein.

d-limonene is a *cannabis* terpenoid, which is known for anti cancer activities (Raphael and Cuttan, J Exp Clin Cancer Res. 2003 September; 22(3):419-24), it is a natural compound found in citrus peel oil, and in *cannabis* leaves. It further is known for its anti inflammatory activity. However, this compound is part of a large number of terpenes which are also produced by *cannabis* plants. These are termed *cannabis* terpenoids and include in non limiting embodiment compounds such as limonene, β-myrcene, α-pinene, linalool, β-caryophyllene, caryophyllene oxide, nerolidol and phytol. These compounds all have various pharmacologically relevant activities, and show synergistic effects with either THC or CBD.

A number of terpenes have been reported to act synergistically with CBD to inhibit inflammation, those includes limonene, β-myrcene, α-pinene.

In a preferred embodiment, limonene, β-myrcene and α-pinene are comprised in the compositions together with CBD for treatment, prevention or alleviation of lung inflammation, by inhalation. In some embodiments, limonene is comprised in the compositions with CBD. In some embodiments, β-myrcene is comprised in the compositions with CBD. In some embodiments, α-pinene is comprised in the compositions with CBD. In some embodiments, β-myrcene and limonene and CBD are comprised in the compositions of the present invention. In some embodiments, β-myrcene, α-pinene and CBD are comprised in the compositions of the present invention.

In some embodiments, limonene, α-pinene and CBD are comprised in the compositions of the present invention. In some embodiments according to anyone of the above embodiments, the compositions may further comprise THC.

In some embodiments, the compositions according to any one of the embodiments of the present invention is for treatment, prevention or alleviation of lung inflammation, wherein the compositions comprise 1.8-cineole alone or together with one or more of the compounds selected from the list of CBD, THC, limonene, β-myrcene, myrcenol, nerol, α-pinene, linalool, β-caryophyllene, indomethacin, caryophyllene oxide, nerolidol, peppermint oil, 1-menthol, menthone, neomenthol, thymohydroquinone, thymol, thymoquinone and phytol. In one embodiment wherein the composition is for treatment, prevention or alleviation of lung inflammation, the composition comprises one or both of 1,8-cineole and limonene.

In some embodiments, the compositions according to the invention is for treatment, prevention or alleviation of an inflammatory disorder of the lungs, and comprises at least one terpene such as at least one terpene selected from the list of a total terpene extract from *Cannabis sativa*, 1.8-cineole, d-limonene, β-myrcene, myrcenol, nerol, α-pinene, linalool, β-caryophyllene, indomethacin, caryophyllene oxide, nerolidol, peppermint oil, 1-menthol, menthone, neomenthol, thymohydroquinone, thymol, thymoquinone, phytol, borneol, camphor, citral, geramol, farnesol and delta3Carene.

In some embodiments, the compositions according to the invention are for treatment, prevention or alleviation of an inflammatory disorder of the lungs, and comprises CBD and/or THC.

In some embodiments, the compositions according to the invention are for treatment, prevention or alleviation of an inflammatory disorder of the lungs, and comprises CBD and/or THC and at least one terpene.

In some embodiments, the compositions according to any one of the embodiments of the present invention is for treatment, prevention or alleviation of lung cancer or cancer in the CNS, wherein the compositions comprise 1.8-cineole alone or together with one or more of the compounds selected from the list of CBD, THC, limonene, β-myrcene, α-pinene, linalool, β-caryophyllene, caryophyllene oxide, nerolidol and phytol.

In some embodiments, the compositions according to the invention are for treatment, prevention or alleviation of lung cancer or cancer in the CNS, and comprises at least one terpene, such as at least one terpene selected from the list of a total terpene extract from *Cannabis sativa*, 1.8-cineole, d-limonene, β-myrcene, α-pinene, linalool, β-caryophyllene, caryophyllene oxide, nerolidol, phytol, borneol, citral, indomethacin and geramol.

In some embodiments, the compositions according to any one of the embodiments of the present invention are for treatment, prevention or alleviation of lung cancer or cancer in the CNS, wherein the compositions comprises CBD and/or THC.

In some embodiments, the compositions according to any one of the embodiments of the present invention are for treatment, prevention or alleviation of lung cancer or cancer in the CNS, wherein the compositions comprises CBD and/or THC and at least one terpene.

However, although many compounds present in *cannabis* have beneficial effects, the normal intake of these compounds by smoking is highly harmful to the lungs, due to the smoking particles and the toxic gasses and the tar. The present invention solves this problem by delivering the ingredients without combustion or powders or toxic chemicals.

In some embodiments, the compositions of the present invention comprise one or more *Cannabis* terpenoids. In some embodiments, the compositions of the present invention comprise one or more monoterpenes. In some embodiments, the compositions comprise one or more diterpenes. In some embodiments the compositions comprises one or more triterpenes.

In some embodiments, the compositions of the present invention comprise total terpene extract from *cannabis* plants. In some embodiments the compositions of the invention comprise a combination of CBD and one or more terpenes selected from mono-, di-, or tri-terpenes. In some embodiments the compositions of the invention comprise a combination of CBD and total terpene extract from *cannabis* plants. In some embodiments, the compositions of the invention comprise a combination of CBD and a terpene selected from total terpene extract from *cannabis*, a mono-, di-, or tri-terpene, in combination with a carrier such as in non-limiting example a peppermint oil.

Non-limiting examples of terpenes that are useful in the present invention: Anethole, has been shown to have analgesic potential in an animal model of pain. α-Bisabolol is the primary constituent (up to 50%) of the essential oil from German chamomile. It has shown anti-aging, anti-irritant, anti-inflammatory, antimicrobial, analgesic, antibiotic and anticancer activities.

Borneol, has been shown to reduce nociceptive behaviour and also to possess anti-inflammatory activities (Almeida et al. The Scientific World Journal, Volume 2013, Article ID 808460, 5 pages). Borneol in addition has shown promise as a treatment for chronic pain, such as inflammatory or neuropathic pain (Jiang et al. Eur J Pharmacol. 2015 Jun. 15; 757:53-58).

Camphor has been shown to inhibit heat induced pain in an animal model, in combination with 1.8-cineole, and α-pinene (Raskovic et al. European Review for Medical and Pharmacological Sciences, 2015; 19: 165-172).

β-caryophyllene and caryophyllene oxide, has shown potential as oral administered drug to treat inflammatory and neuropathic pain in animal models (Klauke et al. European Neuropsychopharmacology (2014) 24, 608-620). Further, in combination with Docosahexaenoic Acid (DHA) showed improved effect on chronic pain states in animal models, with fewer side effects (Fiorenzani et al. 2014 Evidence-Based Complementary and Alternative Medicine, Volume 2014, Article ID 596312, 12 pages).

1.8-cineole has been shown to inhibit heat induced pain in an animal model, in combination with camphor and α-pinene (Raskovic et al. European Review for Medical and Pharmacological Sciences, 2015; 19: 165-172), and an other study indicate an effect of 1.8-cineole on inflammatory and neuropathic pain (Quintao et al Planta Med. 2010 September; 76(13):1411-1418).

Citral is a monoterpene with prophylactic and therapeutic anti-nociceptive effects in experimental models of acute and chronic pain (Nishijima et al. 2014, Eur. J. Pharmacol. August 5; 736; 16-25).

Citronella is a constituent of e.g. essential oil from *Melissa Officinalis* which has been shown to have promise in treatment of inflammation and pain (Bounihi et al. Advances in Pharmacological Sciences, Volume 2013 (2013), Article ID 101759, 7 pages).

Delta-3-Carene, is an anti inflammatory compound which may be extracted from *Cupressus sempervirens* L. Dry leaves of this has been used for treatment of stomach pain. The essential oil from this tree has been used for treatment of headaches (Selim et al. BMC Complementary and Alternative Medicine 2014, 14:179).

Farnesol which is a sesquiterpene alcohol, has been reported to have anti inflammatory activities (Ku and Lin, Food Chem. 2013 Nov. 15; 141(2):1104-13). Further, Farnesol has been tested for and found to have an antinociceptive effect in acetic acid induced writhing test, by de Oliveira Junior et al, who also found that the compound is not neurotoxic at the dosages tested (Fundam Clin Pharmacol 2013 August; 27(4):419-26). Jaggi and Singh has shown a potential for farnesyl or farnesyl derivates in treatment of neuropathic pain (Food Chem Toxicol. 2012 May; 50(5): 1295-1301).

Geraniol, which is the alcohol trans enantiomer of Citral, exhibit the same potential in pain alleviation as citral (Stotz et al. 2008, PLOSone3(5):E2082).

Indomethacin is well known for anti inflammatory activities, as well as for effects on lung cancer or cancer in the CNS in a murine model (Castro et al. Biochem Pharmacol. 2009 Mar. 15; 77(6):1029-39 and Diament et al. Cancer Invest. 2006 March; 24(2):126-31). Furthermore, Indomethacin is marketed as a painkiller. It is used to treat painful conditions such as arthritis, sprains and strains, back pain, period (menstrual) pain, and gout pain.

Isopulegol is part of the essential of e.g. essential oil from *Melissa Officinalis* which has been shown to have promise in treatment of inflammation and pain (Bounihi et al. Advances in Pharmacological Sciences, Volume 2013 (2013), Article ID 101759, 7 pages).

Linalool has shown to be very active against a number of cancer cell types (Cherng et al. Biosci Biotechnol Biochem. 2007 June; 71(6):1500-4), and further attenuates lung inflammation in an animal disease model (Wu et al. Immunopharmacol. 2014 August; 21(2):456-63). Further, linalool has been shown to attenuate allodynia in neuropathic pain, and also to be antinociceptive (Berliocchi et al. 2009; Int Rev Neurobiol 85; 221-235).

Linalyl acetate, has been shown to have anti inflammatory effects (Peana et al. Phytomedicine. 2002 December; 9(8): 721-6), and also significant anti cancer activities ( ). Furthermore, Linalyl acetate was shown by Sakurada et al. to be antinociceptive in an animal model of pain, the capsaicin test (Pharmacol Biochem Behav, 2011 January; 97(3); 436-443), and to inhibit neuropathic hypersensitivity induced by partial sciatic nerve ligation in mice (Kuwahata et al. 2013, Pharmacol Biochem Behav, February; 103(4):735-741). β-myrcene has shown carcinogenic effects, why it is important if using this compound to only use it by local administration, such as directly into the lung. Beta-myrcene has been shown to have anti inflammatory activities (Russo 2011), and potent antitumor effects (Sobral et al. Scientific World Journal. 2014; 2014: 953451). Additionally, β-myrcene showed potential as antinociceptive drug in mice by a low temperature hot plate method and by the acetic acid-induced writhing test (Rao et al, 1990, J Pharm Pharmacol, December; 42(12): 877-878).

myrcenol, is mostly known as a fragrance of lavender, and may serve as a carrier in the present invention.

l-menthol, menthone, menthol and neomenthol, works to reduce inflammation, and may additionally be used as a carrier in the present invention, especially for compositions for use in treatment of lung inflammation.

Nerol oxide is a well known flavour, and may be used as a carrier in the present compositions. Nerol is a major component in essential oil distillates from *Melissa officinalis* L. and experiments with such extracts suggest an effect on inflammation which may lead to pain (Bounihi et al. Adv Pharmacol Sci. 2013; 2013: 101759).

Nerolidol is a naturally occurring terpene in *Cannabis* as well as ginger, jasmine, lavender and tea tree. It has been shown to cause cell cycle arrest and induce apoptosis in hepatucellular cancer cells (Ferreira et al. Toxicology in Vitro, Volume 26, Issue 2, March 2012, Pages 189-196). The compound may also have antiinflammatory effects, and effects on pain, as demonstrated by topical application for skin conditions Oridonin has been shown to inhibit a number of different cancer cell lines, including nonsmall cell lung cancer cells (Ikezoe et al. International Journal of Oncology, Oct. 1, 2003, Pages: 1187-1193), and also have significant effects on inflammatory conditions (Gui et al. BMC Complementary and Alternative Medicine (2015) 15:117).

α-pinene has been shown to inhibit heat induced pain in an animal model, in combination with 1.8-cineole, and camphor (Raskovic et al. European Review for Medical and Pharmacological Sciences, 2015; 19: 165-172).

Peppermint oil is also reported to be anti-inflammatory, and has indeed been used in capsule form for treatment of asthma. It may further be used as a carrier in the present invention.

Phenyl acetic acid and its derivatives, such as Diclofenac, Nepafenac and Bromfenac are well known for their ability to reduce pain and inflammation. Phytol, reduces inflammation (Silva et al., Fundam Clin Pharmacol. 2014 August; 28(4):455-64. Phytol, a diterpene alcohol, inhibits the inflammatory response by reducing cytokine production and oxidative stress). Furthermore, phytol has shown promise as a cytotoxic agent to cancer cells (Pejin et al. Nat Prod Res. 2014; 28(22):2053-6).

Terpineol, in vitro experiments indicate that gamma terpineol inhibits cancer cell proliferation and induces apoptosis (Wu et al. Int J Clin Exp Pathol. 2014; 7(10): 6524-6533). Further, terpineol has shown promising effects in models of lung inflammatory disease such as COPD (Tsou et al. Evidence-Based Complementary and Alternative Medicine, Volume 2014, Article ID 465025).

Terpinen-4-ol, has been shown to have anti inflammatory activities (Ninomiya et al. Biol. Pharm. Bull. 36(5) 838-844 (2013)), and induces apoptosis in human nonsmall cell lung cancer in vivo (Wu et al. Evidence-Based Complementary and Alternative Medicine, page 1-13

Thymol, attenuates allergic airway inflammation in a mouse asthma model (Zhou et al. Fitoterapia. 2014 July; 96:131-7). Thymol protect against radiation induced DNA damage, why thymol is not in the compositions for use in combination with radiation therapy Archana et al Integr Cancer Ther. 2011 December; 10(4):374-83.

Thymoquinone has been shown to have effects on nonsmall cell lung cancer cells when combined with benzo(a) pyrene (APJCP vol 14, issue 10, 2013, Ulasli et al.). Additionally, thymoquinone has been shown to be anti inflammatory (Khader and Eckl, Iran J Basic Med Sci 2014; 17:950-957).

Formulations and Uses

The present invention provides passive inhaler devices comprising compositions with active compounds and one or more carriers. The active compounds such as CBD may be separate from the carrier, or it may be mixed with the carrier. The inhaler device of the invention is for delivery of active substances to anyone of the lungs, the oral mucosa or to the central nervous system, such as to the brain. The inhaler device of the invention is for treatment, prevention or alleviation of inflammatory conditions of the lungs or oral mucosa, or of the central nervous system, such as the brain. In some embodiments, the inhaler device of the invention is for treatment, prevention or alleviation of neurodegenerative diseases. In some embodiments, the inhaler device of the invention is for treatment, prevention or alleviation of chronic cough, in which case, the active compound in the device is a local anaestetic, such as an opioid such as fentanyl or ibuprofen or paracetamol, and the carrier is any carrier, or may be a carrier with an antiinflammatory activity. In some embodiments, the inhaler device of the invention is for treatment, prevention or alleviation of a plaque related disease, such as a neurodegenerative disease, such as any one of alzheimers disease or parkinsons disease. In some embodiments, the inhaler device is for treatment, prevention or alleviation of epilepsy.

In some embodiments, the passive inhaler is for use in treating chronic cough or chronic inflammation of the oral mucosa, in which case the passive inhaler may comprise a local anaestetic, such as an opioid, such as fentanyl, or ibuprofen or paracetamol and a carrier. In some embodiments, where the passive inhaler is for use in treating chronic inflammation of the oral mucosa, the inhaler may comprise ibuprofen or CBD, optionally in combination with an antiinflammatory terpene, and optionally an additional carrier, which may be peppermint oil.

In the present invention, in some embodiments, the passive inhaler is for treatment, prevention or alleviation of any one of Lung inflammation, acute lung injury, COPD or lung cancer or Cancer in the CNS, and may comprise CBD formulated in the device alone with a carrier, or together with an antiinflammatory terpene and optionally an additional carrier, for inhalation into the lungs. In some embodiments, where the passive inhaler is for treatment, prevention or alleviation of Lung cancer or cancer in the CNS, the inhaler comprises CBD and a carrier, and optionally a terpene with anti-cancer activity. In some embodiments, the passive inhaler is for treatment, prevention or alleviation of cancer in the lungs or in the CNS, and comprises CBD and one or more of total terpene extract from *Cannabis sativa*, 1.8-cineole, d-limonene, β-myrcene, α-pinene, linalool, β-caryophyllene, caryophyllene oxide, nerolidol, phytol, borneol, citral, indomethacin and geramol.

In some embodiments the passive inhaler is made for treatment, prevention or alleviation, prevention or alleviation of lung cancer, cancer in the oral cavity or cancer in the central nervous system (CNS). In some embodiments, the passive inhaler is for treatment, prevention or alleviation of lung cancer or cancer in the CNS, such as any one of small cell lung cancer or nonsmall cell lung cancer, cancer in the oral cavity such as head and neck cancer or glioma, or metastasis in the CNS of cancer originating from other organs. In some embodiments, the passive inhaler is for treatment, prevention or alleviation of lung cancer such as any one selected from the list of small cell lung cancer and nonsmall cell lung cancer. In some embodiments, the passive inhaler is for treatment, prevention or alleviation of nonsmall cell lung cancer in any one of stages I, II, III or IV. In some embodiments, the passive inhaler is for treatment, prevention or alleviation of nonsmall cell lung cancer in any one of stages I or II, such as in stage I. In some embodiments, the passive inhaler are for treatment, prevention or alleviation of nonsmall cell lung cancer, wherein the nonsmall cell lung cancer is any one of adenocarcinoma, squamous cell carcinoma or large cell carcinomas. In some embodiments, the passive inhaler of the invention is for use in the treatment, prevention or alleviation of cancer in the oral cavity, such as head and neck cancer. In some embodiments, the passive inhaler of the invention is for use in the treatment, prevention or alleviation of cancer in the CNS, such as glioma or metastases in the CNS from cancer in other parts of the body.

In some embodiments, the passive inhaler is for use in treatment, prevention or alleviation of small cell lung cancer in limited stage or extensive stage. In some embodiments, the passive inhaler is for use in treatment, prevention or alleviation of small cell lung cancer in the limited stage.

In some embodiments, the composition according to the present invention is for use in treatment, prevention or alleviation of lung cancer, including small cell lung cancer and nonsmall cell lung cancer, or for treatment, prevention or alleviation of cancer in the oral cavity, such as head and neck cancer or for treatment, prevention or alleviation of cancer in the CNS, and wherein the composition is for use in combination with radiation therapy and/or chemotherapy.

In some embodiments, the passive inhaler is for treatment, prevention or alleviation of epilepsy, or anxiety or depression or psychosis or schizophrenia, wherein the passive inhaler comprises CBD and a carrier.

In some embodiments, the passive inhaler is for use as an anti-emitic, to prevent vomiting in patients The formulation may be one adapted for delivery from a passive inhaler, or from an inhaler device with only moderate heating as described elsewhere. The inventors have shown that it is possible to deliver CBD as a vapor from a passive inhalator, in some embodiments without heating at all, and in other embodiments, without heating above any one of 60, 70, 80, or 90° C., and in a further embodiment, without heating above a temperature above any one of 140° C., such as above 150° C., such as above 160° C., such as above 170° C. or such as without heating above 180° C.

Carriers

In one embodiment, the CBD or THC or composition of active compound may be formulated with a carrier, such as peppermint oil or other vegetable oil with a flavour. In one embodiment, the composition of the present invention is formulated in a passive inhaler device comprising an anti-inflammatory terpene as a carrier. In one such embodiment, the terpene used as a carrier is one or more of borneol, camphor, β-caryophyllene, caryophyllene oxide, 1,8-Cineole, citral, Delta3Carene, geraniol, indomethacin, limonene, linalool, linalyl acetate, (3-myrcene, myrcenol, 1-menthol, menthone, neomenthol, nerol, nerolidol, α-pinene, peppermint oil, Pulegone, phytol, Terpineol, Terpinen-4-ol, thymohydroquinone, thymol, thymoquinone. In one embodiment, a terpene may be used as a carrier in combination with use of another carrier such as peppermint oil or another flavoured vegetable oil.

In one embodiment, the composition of the present invention is formulated in a passive inhaler device with an anti-cancer acting terpene as a carrier. In one such embodiment, the anti-cancer terpene used as a carrier is one or more selected from the list of, d-limonene, α-pinene, nerolidol, indomethacin and geramol, borneol, camphor, β-caryophyllene, caryophyllene oxide, 1,8-Cineole, citral, Delta3Carene, geraniol, indomethacin, limonene, linalool, linalyl acetate, (3-myrcene, myrcenol, 1-menthol, menthone, neomenthol, nerol, nerolidol, α-pinene, peppermint oil, Pulegone, phytol, Terpineol, Terpinen-4-ol, thymohydroquinone, thymol, thymoquinone In one embodiment, the composition of the present invention is formulated in a passive inhaler device with a terpene or another carrier such as a tobacco extract, or caffeine, or cocoa terpenes, or coffee terpenes, which will increase local transport of substances across the blood brain barrier.

Examples of useful carriers are those of terpenes derived from *Cannabis*, or total terpene extract from *Cannabis* plants, terpenes from coffee or cocoa. Mint, Eucalyptus, Citrus, tobacco extracts of Virginia, Burley, Caquito, Nicaragua etc. Anis, propylene glycol, ethanol, water, oxygen, nitrogen, normal air, sodium chloride, peppermint oil.

Terpenes selected from the list of d-limonene, β-myrcene, α-pinene, linalool, geramol, Anethole, α-Bisabolol, Borneol, Camphor, β-caryophyllene and caryophyllene oxide, 1.8-cineole, Citral, Citronella, Delta-3-Carene, Farnesol, Geraniol, Indomethacin, Isopulegol, Linalool, Linalyl acetate, β-myrcene, myrcenol, 1-menthol, menthone, menthol and neomenthol, Nerol oxide, Nerol, Nerolidol, Oridonin, α-pinene, Peppermint oil, Phenyl acetic acid and its derivatives, such as Diclofenac, Nepafenac and Bromfenac, Phytol, Terpineol, Terpinen-4-ol, Thymol, Thymoquinone may also be used as carriers in the present invention.

Device for Delivery of the Compositions of the Invention:

In one embodiment, the invention is a passive inhalator or other device useful for delivering compositions in the oral cavity or nose or to the lungs as a gas, or a vapor or a mist or an aerosol without heating, wherein the device or passive inhalator comprises the compositions of the invention. A passive inhalator is a device which allows for the compositions of the invention to be delivered without excessive heating, such as without heating above a temperature above any one of 140° C., such as above 150° C., such as above 160° C., such as above 170° C. or above 180° C., such as without heating above any one of 60° C., 70° C., 80° C., or 90° C. without heating at all. One example of such a device is described below.

In some embodiments, a passive inhaler is an inhaler without any heating. In some embodiments, a passive inhaler is an inhaler without heating the ingredients above any one of 60, 70, 80, or 90° C. In some embodiments, a passive inhaler is an inhaler without heating the ingredients above any one of 140° C., such as above 150° C., such as above 160° C., such as above 170° C. or such as without heating the ingredients above 180° C.

Examples of Devices for Delivery of the Compositions as a Vapor

It has not previously been shown that CBD compositions may be delivered to the lungs as a vapor or a gas using a passive inhalator device. In one preferred embodiment, the compositions, methods and uses of the present invention are for use with a passive inhalator device. Such devices may have various designs, and in non limiting example they may be such as those or similar to those disclosed in WO2011107104 (hereby included by reference) or those disclosed in PCT/DK2013/000051.

An improved device may also be used in the present invention, which in principle is similar to the device disclosed in WO2011107104, but to which means are introduced to increase the availability of the carrier, and to avoid escape of the carrier from the device if the user sucks from the wrong end of the device.

In one embodiment, a hard porous plastic (or similar) filter is placed between the ball and the pin shaped release device. This filter will prevent escape of the carrier or other substance from the device, and will be able to absorb the carrier, and thereby, due to the increased exposure area, provide increased efficiency of the delivery of substances from the device. The pore size may be varied to increase the resistance, or to increase or decrease the evaporation of the absorbed substance. Further, the hardness of the filter may be adjusted in order to avoid penetration by the release device, or built into the release device, or the release device is a hard filter.

The filter may in some embodiments be of a hardness which allow the inhaler to be activated.

In some embodiments the filter may be between 1 mm and 40 mm long. In some embodiments, the filter may have a pore size of between 0.01 micrometer and 10 micrometer. The filters or device may be produced with groves to regulate airflow and flowdrop.

In one embodiment, the device may comprise a porous or acetate filter in the inhalation part, in order to prevent materials to escape from the inhalation device. This porous filter may be integrated in the central air passage of the existing barrier, e.g. star shaped barrier in the inhalation part. The porous filter may be separate from the barrier.

The filter may be between 1 mm and 20 mm long.

In some embodiments, it is preferred that there also is an increased area at which the carrier may pick up the active pharmaceutical ingredient (API) (in this case CBD). This may be achieved by making the ball in the inhalation part smaller than the ball in the middle. In this way, the device may be designed to allow passage of the API past the ball, and to be absorbed by the filter. When the carrier passes through the first compartment and the filter, it will take up the API with increased efficiency. This filter may in one non limiting embodiment consist of a normal acetate filter.

This improved device allows for improved efficacy of delivery, by higher concentration of API and carrier in the inhaled air from the device, as well as avoidance of escape of fluids and materials from the device.

It is important that the material of which the filters are made will not absorb the substances comprised in the device, such as the carriers and the API. It is also important that the filters have a pore size that allows air to be readily puffed through the filter by the user. Also, the filter material must be of a kind that will not release unwanted compounds from the filter material during use.

In non-limiting example, the filters may be made of polypropylene (PP) or polyurethane (PUR), or the like.

In one embodiment, a porous filter may also be placed between the balls, to create distance between the balls during production process and activation process and for the purpose of separating the API and the carriers after activation.

In some embodiments, (See FIG. 2. Detail C: C-100) a heating VAVE device CAP may be attached to the device which is activated when air is sucked into the device, and which will heat the air which is sucked into the device to a temperature not exceeding any one of 60, 70, 80, or 90° C., and in a further embodiment, without heating above a temperature above any one of 140° C., such as above 150° C., such as above 160° C., such as above 170° C. or above 180° C. In other embodiments, no heating device is attached or connected to the passive inhaler device used for delivery of the compositions of the present invention.

In some embodiments, the vapor or gas or mist or aerosol created from the compositions of the present invention are delivered by positive airway pressure. In some embodiments, the present invention is a passive inhaler device comprising the compositions of the present invention.

Dosages

Relationship between components of the present invention—CBD/THC/terpenes vs carriers. In some embodiments, the passive inhaler device comprises active compounds such as CBD, THC, tobacco extracts and/or terpenes in a 1:1 relationship with a carrier, such as peppermint oil. In some embodiments, the relationship between the active compound and the carrier may be within the range of between 5:1 and 1:5, such as between 4:1 and 1:4, such as between 3:1 and 1:3, such as between 2:1 and 1:2, such as about 1:1.

Dosages in the Passive Inhaler Device.

The actual dosage received in the body is what matters. Depending on which device is used, the actual amount of active compound and carrier present in the device may vary, and given the knowledge from the present invention, that these compounds may be delivered to the lungs in pharmaceutically relevant dosages without excessive heating, is without any undue burden to adjust the dosage in a given device to achieve a desired delivery of active compound into the lungs.

In some embodiments, the compositions of the invention are made to deliver between 0.1 mg to 15 mg active compound to the lungs or to the mucosa of the oral cavity (for transport to the brain) over a period of 1-6 hours. In some embodiments, the composition of the invention are made for delivery of 0.1 mg to 15 mg CBD and/or THC into the lungs or mucosa of the oral cavity over a period of 1-6 hours.

In some embodiments, a dosage of between 0.1 and 50 mg of one or more terpenes are delivered into the lungs or to the mucosa of the oral cavity over a period of 1 to 6 hours. In some embodiments, patients are administered the compositions of the invention 2 times per day for 1 to 6 hours.

In some embodiments, the compositions of the invention are administered to a patient for periods of one week at a time interrupted by a pausing during which a doctor may inspect the status of disease.

In some embodiments, the invention is a passive inhaler device comprising CBD and a carrier, wherein the CBD is between 1 and 80% pure (by weight). Such as between 1 and 75%, such as between 10 and 75%, such as between 20 and 75%, such as between 25 and 70% pure.

In some embodiments, the passive inhaler device of the invention comprises a total of between 1 and 75% by weight CBD, such as between 10 and 70% CBD, such as between 10 and 60% CBD, such as between 10 and 50% CBD, such as between 15 and 40% CBD.

Method of Treatment

The present invention provides a method of treatment, wherein the passive inhaler comprising the compositions of the invention is used for delivering gaseous or vapor or mist forms of the composition to the mucosa of the oral cavity or to the lungs to facilitate delivery of the composition to the CNS and thereby treat neurodegenerative diseases, such as any one of plaque related disorders of the CNS, such as parkinsons disease, alzheimers disease, schizophrenia, transmissible spongiform encephalopathy, bovine spongiform encephalopathy, huntingtons disease, Familial amyloid polyneuropathy, Finnish amyloidosis, Lattice conical dystrophy, cerebral amyloid angiopathy, cerebral amyloid angiopathy Icelandic type.

The present invention also provides a method of treatment, wherein the passive inhaler comprising the compositions of the invention is used for delivering gaseous or vapor or mist forms of the composition to the mucosa of the oral cavity or to the lungs to facilitate delivery of the composition to the CNS and thereby treat diseases selected from the list of psychosis, anxiety, depression, emitic conditions such as any one of motion sickness, side effects of opioid analgesics, side effects of general anaesthetics, side effects of chemotherapeutics, morning sickness, severe cases of gastroenteritis.

The present invention also provides a method of treatment, wherein the passive inhaler comprising the compositions of the invention is used for delivering gaseous or vapor or mist forms of the composition to the mucosa of the oral cavity or to the lungs to facilitate delivery of the composition to the CNS and thereby treat diseases selected from the list of tumours in the central nervous system (CNS), such as any one of glioblastoma, metastases of tumors originating from other parts of the body, such as from Lung cancer, breast cancer, genitourinary tract cancers, osteosarcoma, melanoma, head and neck cancer, neuroblastoma, gastrointestinal cancers, colorectal carcinoma, pancreatic carcinoma and lymphoma. In some embodiments, the method of treatment for cancer in the CNS is for use in combination with radiation therapy, or in combination with chemotherapy or both.

In some instances, the methods of treatment of the present invention is for treatment of patients which do not respond to treatment with for example CBD or a combination of CBD and THC when administered orally, systemically or by smoking.

In some embodiments, the methods of treatment of the present invention are methods for enhancing transport of substances across the blood brain barrier. In some embodiments, the passive inhaler device of the invention comprises flavours or compounds which increase permeability of the blood brain barrier, and thereby allows for increased transport or diffusion of substances, such as of medicaments which do not normally cross the blood brain barrier in sufficient amount in order to have an optimal effect on a brain target. Such compounds may be in non limiting example any one or more of a mono-, di- or a tri-terpene, a terpene, a tobacco flavour, or a compound known for increasing metabolism such as caffeine or nicotine. By delivering the compounds with the device via the oral mucosa, the effect on the permeability of the blood brain barrier will remain local, and will not cause a general change in permeability of the whole blood brain barrier.

The present invention thus provides a method of increasing permeability of the blood brain barrier to make compounds present in the blood circulation able to cross the blood brain barrier and enter the cerebrospinal fluid and be transported to its brain target. In other embodiments, the present invention provides a method of increasing permeability of the blood brain barrier to allow compounds, such as amyloid or tau proteins to exit the brain and be transported away by the blood circulation system.

Uses of the Invention

The passive inhaler device of the invention comprising the compositions of the invention is for use as a medicament. In some embodiments, the passive inhaler device of the invention comprising the compositions of the invention is for use in the treatment of any one of a neurodegenerative disease, such as any one of plaque related disorders of the CNS, such as parkinsons disease, alzheimers disease, schizophrenia, transmissible spongiform encephalopathy, bovine spongiform encephalopathy, huntingtons disease, Familial amyloid polyneuropathy, Finnish amyloidosis, Lattice corneal dystrophy, cerebral amyloid angiopathy, cerebral amyloid angiopathy Icelandic type.

In some embodiments, the passive inhaler device of the invention comprising the compositions of the invention is for use in the treatment of any one of the diseases selected from the list of psychosis, anxiety, depression, emitic conditions such as any one of motion sickness, side effects of opioid analgesics, side effects of general anaesthetics, side effects of chemotherapeutics, morning sickness, severe cases of gastroenteritis.

In some embodiments, the passive inhaler device of the invention comprising the compositions of the invention is for use in the treatment of any one of the diseases selected from the list of tumours in the central nervous system (CNS), such as any one of glioblastoma, metastases of tumors originating from other parts of the body, such as from Lung cancer, breast cancer, genitourinary tract cancers, osteosarcoma, melanoma, head and neck cancer, neuroblastoma, gastrointestinal cancers, colorectal carcinoma, pancreatic carcinoma and lymphoma. In some embodiments, the passive inhaler device of the invention comprising the compositions of the invention for is for use in treatment of cancer in the CNS in combination with other treatment, such as for use in combination with radiation therapy, or in combination with chemotherapy or both.

In some embodiments, the passive inhaler device of the invention comprising the compositions of the invention is for use in the treatment of patients which do not respond to treatment with for example CBD or a combination of CBD and THC administered orally, systemically or by smoking.

In some embodiments, the passive inhaler device of the invention comprising the compositions of the invention is for enhancing transport of substances across the blood brain barrier. In some embodiments, the passive inhaler device of the invention comprises flavours or compounds which increase permeability of the blood brain barrier, and thereby allows for increased transport or diffusion of substances, such as of medicaments which do not normally cross the blood brain barrier in sufficient amount in order to have an optimal effect on a brain target. Such compounds may be in non limiting example any one or more of CBD, a mono-, di- or a tri-terpene, a terpene, a terpenoid, a tobacco flavour, or a compound known for increasing metabolism such as caffeine or nicotine. By delivering the compounds with the device, the effect on the permeability of the blood brain barrier will remain local, and will not cause a general change in permeability of the whole blood brain barrier.

The present invention thus provides a method of increasing permeability of the blood brain barrier to make compounds present in the blood circulation able to cross the blood brain barrier and enter the cerebrospinal fluid and be transported to its brain target. In other embodiments, the present invention provides a method of increasing permeability of the blood brain barrier to allow compounds, such as amyloid or tau proteins to exit the brain and be transported away by the blood circulation system.

Production of CBD

Many different extraction methods for extracting CBD are known in the art. In some methods, heat is used to distill the CBD which has a boiling point of 160-180 degrees C. Some CBD extraction methods are performed at lower temperatures, and include, but not limited to alcohol extraction, CO2 extraction and oil extraction (e.g. olive oil). The skilled person would know from the art how to perform such methods, to extract CBD useful in the present invention. CBD for use in the present invention, may be extracted in some embodiments, to still comprise natural terpenes from the *Cannabis* plant, and in some embodiments, the CBD does not comprise terpenes, or only small amounts of terpenes (such as less than 10% terpenes, such as less than 9% or less than 8% or less than 7% or less than 6% or less than 5% or less than 4%, or less than 3% or less than 2% or less than 1% terpenes when compared to the amount of CBD in the extract as measured by weight).

In some embodiments, the CBD extracts when mixed with carriers, for use in the present invention comprises between 1 and 80% CBD as measured by weight of CBD compared to total weight of the extract. In some embodiments, the concentration of CBD is between 20% and 80%, such as between 25% and 80%, such as between 10% and 60% CBD, such as between 5% and 75% CBD, such as between 15% and 50%, such as between 20% and 40% CBD.

Passive Inhaler with CBD Extract and Carrier

The present invention provides passive inhalers loaded with CBD extract. In some embodiments, the passive inhaler with the CBD extract further comprises one or more carriers.

A passive inhaler according to the present invention is an inhaler device capable of delivering the CBD as a vapor to the oral cavity or lungs, when formulated with a carrier in the inhaler device. The CBD extract and the carrier may be contained in different compartments in the device, or they may be formulated together.

Non limiting examples of passive inhalers which may be used in the present invention are those disclosed in WO2011107104 (hereby included by reference) or those disclosed in PCT/DK2013/000051 (included by reference). Further, in non-limiting example, the device described above may be used as the device comprising CBD and carriers as claimed in the present invention.

BRIEF DESCRIPTION OF THE DRAWINGS

Delivery and improved device.

In FIG. 1. Drawings show a VAVE Device with mouthpiece before the pinn/plounger (F) is pushed into the tube.

The one drawing (AA-1) show the device from outsite/showing the look and outer surfaces.

The one drawing (AA-2) show the device as a cut longitude through the device, open look, insite the device, turned 45 degrees to also show the mouthpiece part insite (see E-10)

In FIG. 2. Drawings show a VAVE Device with CAP (see detail B-100 and CAP (27)) and mouthpiece (see detailE-100) after the pinn/plounger (F) is pushed into the tube.

The one drawing (BB-1) show the device as a cut longitude through the device, open look, insite the device. (See counter and batterie, E.100)

The one drawing (BB-2) show the device as a cut longitude through the device, open look, insite the device, turned 45 degrees to also show the mouthpiece part insite in turned angle.

DETAILED DESCRIPTION OF THE INVENTION

The compositions of the present invention, for delivery via the nasal passage to the brain, may be delivered by various means known in the art, to provide the composition in a form which will be absorbed through the membranes in the back of the nose or the oral mucosa. In some embodiments, the passive inhaler device of the invention is anyone of the devices described below, or in WO2011/107104, or similar to those.

In one embodiment, such delivery may be by use of a device similar to that disclosed in WO2011/107104 (WO2011/107104 included by reference), in which 3 balls separate carrier from the active pharmaceutical ingredient (API). The present invention further provides a device which is improved in comparison to the device disclosed in WO2011107104. This improved device provides means to increase availability of the carrier, and to avoid carrier escaping the device if the user suck from the wrong end of the device, as well as means to avoid escape of material such as API or tobacco and/or marihuana leaves etc. from the device in the end at which the user puffs from.

In one embodiment, a hard porous plastic (or similar) filter (A-100) is placed between the ball and the pin shaped release device. This filter will prevent escape of the carrier or other substance from the device, and will be able to absorb the carrier, and thereby, due to the increased exposure area, provide increased evaporation of the carrier. The increased evaporation of carrier will allow an increased efficiency of the delivery of substances from the device. The pore size may be varied to increase the resistance, or to increase or decrease the evaporation of the absorbed substance. Further, the hardness of the filter may be adjusted in order to avoid penetration by the release device. In one embodiment, the filter is attached to the release device, or is built into the release device, or the release device is a hard filter.

The filter (A-100) may in some embodiments be of a hardness which allow the inhaler to be activated.

In some embodiments, the filter (A-100) may be between 1 mm and 40 mm long.

In some embodiments, the filter (A-100) may have a pore size of between 0.01 micrometer and 10 micrometer. Produced with groves to regulate airflow and flowdrop.

In one embodiment, the device may comprise a porous or acetate filter (D) in the inhalation part, in order to prevent materials to escape from the inhalation device. This porous filter may be integrated in the central air passage of the existing barrier, e.g. star shaped barrier in the inhalation part. The porous filter (D) may be separate from the barrier.

The filter (D) may be between 1 mm and 20 mm long.

In some embodiments, it is preferred that there also is an increased area at which the carrier may pick up the API. This may be achieved by making the ball in the inhalation part smaller than the ball in the middle. In this way, the device may be designed to allow passage of the API past the ball, and to be absorbed by the filter (D-100). When the carrier passes through the first compartment and the filter (D-100), it will take up the API with increased efficiency. This filter (D-100) may in one non limiting embodiment consist of a normal acetate filter.

This improved device allows for improved efficacy of delivery, by higher concentration of API and carrier in the inhaled air from the device, as well as avoidance of escape of fluids and materials from the device.

It is important that the material of which the filters are made will not absorb the substances comprised in the device, such as the carriers and the API. It is also important that the filters have a pore size that allows air to be readily puffed through the filter by the user. Also, the filter material must be of a kind that will not release unwanted compounds from the filter material during use.

In non-limiting example the filter (A-100) and/or filter (D-100) may be made of polypropylene (PP) or polyurethane (PUR), or the like.

In one embodiment, a porous filter may also be placed between the balls, to create distance between the balls during production process and activation process and for the purpose separating the API and the carriers after activation.

The improvements in the device may also be described as follows:

(A-100): Hard PUR/PP etc. Stopfilter (A-100) Dose controle, Airflow and flowdrop improvement:

The hard PUR filter, (A-100), between the last inserted ball and the pin/plounger (F-100), enlarges the surface of the carriers and absorbing the carriers while moving the plounger (F-100) into the device for activation. Its function is also to stop liquids floating from the device and to keep the separation of the substances after activation. The function of this filter is also to bring possibility for the consumer to puff from both points of the device, without sucking the liquid extracts/substances into the mouth, as if this was a straw.

The function of this filter is also to push the 3 sealing bodies and the substances between these bodies into the first compartment, without collapsing, in a way, to stay partly in the second compartment partly in the first compartment or between these two compartments, after the activation process. This is to assure the use of the expanded area that the substances are vaporizing from and to controle the liquids in the device to stay away from the plounger point (F-100), opposite the mouthpiece point (E-10) and (E-100).

DETAIL: (B) & (C) CAP improvement, dose controle:

A solution with the cap(27). DETAIL B, added to open for solutions (C-10) that can bring different dosing controlling abilities to this improved device, such as electronic counters, electronic blinking lights, that can be in green turning to red, after a number of puffs of the right pressure, delivering the fixed needed dose per puff, depending on the nature of API that this device delivers.

Cap (27), that can have the feature incorporated Heat-flaps:on/off & battery (C-100), connected with the technology in the mouthpiece and incorporated technology with light(s) or whistle(s) to bring signals to the consumer when to stop further intake, after receiving full dose.

Accessories can make devices look in the way, that consumers need, to "take the medicine" The cap solution is a way to improve the device in a way, that brings the consumer into a more acceptable lifestyle, while consuming the needed treatment.

The cap solution improves the feasibility of activating the device more easy. It also shows from where to puff, having the mouthpiece in the one point.

The cap can be designed in different designs and colors and materials, as long as it is designed to hold the inhaler inside, in a way to provide air passing through, when inserted and activated.

(D-100) Soft Acetate Etc. Improvement:

The soft filter, (D-100), to be inserted in the position in the inhalation part of the device. This filter avoids particles to pass through the star hole and absorbs the API to enlarge the surface for volatile "delivering" the liquid API as a gas, with or without being picked up by volatile carriers, that is physically moved by air containing water vapor, nitrogen, oxygen, argon, carbon dioxide, neon, helium, krypton, hydrogen, xenon and different particles from the area, that can be particles from environmental character or pollution, like in cities we find high concentration of diesel combustion, charcoal combustion, smoking particles, combustion particles from chimneys etc. airborne latex allergens, allergenic proteins etc. and these particles can be from nature like hay fever from grass, pollinosis from pollens of any plant, animal dander etc.

This filter can be produced from supplier directly in connection with different fermented and cutted tobacco or marihuana etc. leaves together with the starhole filter. (G-10).

Mouthpiece Improvement:

The mouthpiece, (E-10) and nose/mouth piece (E-100), invented provides a stop solution barre, for the purpose to avoid ricecorns, different plant leaves etc to pass through the star hole in the filter of the device/improved inhaler, in a way, that the particle is dirigated to stay in the mouthpiece.

This mouthpiece can be constructed including electronic counter, figures to provide the consumer with informations regarding the dosage, passing through the device. This electronic counter technology can be separated from or connected with the Cap (27), that can have the feature incorporated battery, connected with the technology in the mouthpiece and incorporated technology with light(s) or whistle to bring signals to the consumer when to stop further intake, after receiving full dose.

This mouthpiece can also be constructed to be used for the purpose delivering the vapor nasally. (see E-100)

This way its designed as a double tube "nosemouthpiece" (E-100) added to this inventions improved device, and can be a part of this invention.

Endpoints and Markers

Effects of the treatments presented in the invention relating to lung inflammation, may be in non limiting example measured as improvements of various disease markers. In non-limiting example, such markers may include any one of an inflammation marker selected from the list of C-reactive protein (CRP), soluble tumour necfosis factor-receptor (TNFR-1), osteoprotegerin (OPG) and monocyte chemoattractant protein-4 (MCP4) (Eagan et al. 2010 European Respiratory Journal vol 35 no 3 p 540-548). Other objective indications of improvement, such as improvement in a disease symptom may also be taken as measurement for effect. One effect by which effect may be measured is general well being, mucus coughing coloured with e.g. tar particles. Improvement in ease of breathing.

Effects of the treatments presented in the invention relating to lung cancer or cancer in the CNS, may in non limiting example be measured as improvements of various disease markers. In non limiting example, this may be proliferation arrest, prevention of spreading of disease into other tissues, shrinking of tumor mass.

Effects of the treatments presented in the invention relating to epilepsy, may in non limiting example be measured by reduction in severity of attacks or fewer attacks.

Effects of the treatments presented in the invention relating to the use of the passive inhaler as an anti-emetic, may in non limiting example be measured by reduction in vomiting, or in the sensation of nauseaness.

Effects of the treatments presented in the invention relating to the use of the passive inhaler to treat anxiety, depression or psychosis, may be measured by a reduction in the symptoms of those diseases.

Effects of the treatments presented in the invention relating to use of the passive inhaler to treat neurodegenerative diseases, may be measured by observing a slowing down of the decline in neurological function.

EXAMPLES

Example 1

The compositions and methods of the invention will be tested in relevant animal models of inflammatory lung diseases, including models of acute lung injury and COPD.

Various dosages of CBD will be delivered to the lungs by use of passive inhaler devices comprising different dosages of CBD and a carrier to identify the optimal dosage range.

Example 2

In some applications, nicotine may be used in the inhaler. Nicotine may be delivered in three forms with tobacco flavours:

A: As dried fermented tobacco leaves in cut form (this form will provide a stimulus to the brain similar to that of natural tobacco flavours as seen when smoking)

B: As heat (247 degree Celcius) or high pressure distilled extract made by a 7 phase distillation process, wherein the extract comprises nicotine and possibly some tobacco flavours.

C: As a blended mass of tobacco leaves, extracted by nut oil, tasteless oil or propylene glycol. In some instances it may be washed with $CO_2$ or ethanol in the aromaextraction process. The composition is mixed with the composition of B), and leaf parts are removed by pouring through a cloth or the like. The resulting fluid will be uniform and volatile and able to release its natural tobacco flavours Example 3

CBD extraction from *Cannabis* plants is done similar to nicotine extraction from tobacco as described in example 2.

CBD is extracted at 250 degrees Celcius.

Cannabidiol (CBD) has a boiling point of: 160-180 degrees C./320-356 degrees Fahrenheit CBD may also be extracted by other methods, such as $CO_2$ extraction, Ethanol or olive oil extraction:

$CO_2$ extraction. The supercritical (or subcritical) $CO_2$ method uses carbon dioxide under high pressure and extremely low temperatures to isolate, preserve, and maintain the purity of the medicinal oil. This process requires expensive equipment and a steep operational learning curve. But, when done well the end product is safe, potent, and free of chlorophyll.

Ethanol. High grade grain alcohol can be used to create high quality *cannabis* oil appropriate for vape pen cartridges (E-cigarettes using heating) and many other products. But this extraction method destroys the plant waxes, which may have health benefits that are favored by some product-makers.

Olive oil. Extra virgin or otherwise, olive oil can also be used to extract *cannabis* oil. Dr. Arno Hazekamp, director of phytochemical research at Bedrocan BV, which supplies medical *cannabis* for the Dutch Health Ministry, reports this method is both safe and inexpensive, "You won't blow yourself up making *cannabis*-infused olive oil." *Cannabis*-infused olive oil—whether CBD-rich or THC-dominant—is however perishable and should be stored in a cool, dark place.

Properties: Anxiolytic, Analgesic, Antipsychotic, Antiinflammatory,

Antioxidant,

Antispasmodic

Properties of other *cannabis* compounds:

Cannabinol (CBN)

Boiling point: 185° C./365 degree Fahrenheit

Properties: Oxidation, breakdown, product, Sedative, Antibiotic

Cannabichromene (CBC)

Boiling point: 220° C./428 degree Fahrenheit

Properties: Antiinflammatory, Antibiotic, Antifungal

Δ-8-tetrahydrocannabinol (Δ-8-THC)

Boiling point: 175-178° C./347-352.4 degree Fahrenheit

Properties: Resembles Δ-9-THC, Less psychoactive, More stable Antiemetic

Tetrahydrocannabivarin (THCV)

Boiling point: <220° C./<428 degree Fahrenheit

Properties: Analgesic, Euphoriant

Example 4

In some instances, it will be advantageous to supplement treatment of the present invention with systemic treatment with CBD. For this purpose CBD in capsule form up to a maximum of 100-200 mg daily, preferably 100 mg daily, may be administered.

CBD in capsule form, may be delivered via the gastro-intestinal tract.

Example 5

10 COPD patients were given a device comprising 8.6 mg CBD and peppermint oil to a total of about 75 mg.

The patients took 200 puffs in about 4-6 hours, wherein the patients took one puff through the device and included the air from that one puff in each breath of air that was taken into the lungs. This procedure was continued for 4-6 hours.

Result: the patients felt an improved well being, they coughed up black mucus, and felt an improved ease of breathing.

Example 6

10 COPD patients will be given a device comprising 8.6 mg CBD and a 50:50 mixture of peppermint oil and total *Cannabis sativa* terpene extract to a total of about 75 mg.

The patients will take 200 puffs in about 4-6 hours, wherein the patients took one puff through the device and included the air from that one puff in each breath of air that was taken into the lungs. This procedure was continued for 4-6 hours.

Some patients will be given two times 200 puffs per day, and some will be given only 200 puffs per day.

Some patients will as a control be given the CBD/peppermint oil device of example 5.

Example 7

A patient suffering from multiple sclerosis experiencing continuous pain, which he normally only can treat by smoking of *cannabis*, which has the side effect of making him constantly under influence by the drug, and thereby being mentally sedated in addition to the effect on the pain. The patient does not respond to CBD gel capsules when taken orally, and is thus a non-responder to oral CBD.

The patient tested the passive inhaler devices of the invention loaded with three different compositions:
1) Negative control only loaded with peppermint oil as a carrier.
2) Positive loaded with CBD and peppermint oil, wherein the concentration of the CBD initially was 61%, and after mixing with carrier (peppermint oil), the final concentration of CBD was 30% by weight.
3) Positive loaded with CBD (31%) and carrier (peppermint oil), the final concentration of CBD was 15% by weight.

The patient experienced severe pain in the legs and feet, and the sensation of pain was not influenced by inhaling the negative control after about 15 minutes of puffing on device number 1. The patient however responded to both inhaler number 2 and 3. His response to inhaler number 3 was partial, as he after puffing on device number 3 for about 12 minutes, he still experienced moderate pain, but described the effect as good. Device number 2 with 30% CBD by weight had the best effect, it removed so much pain that the patient did no longer have to use energy to control his pain. This effect appeared after about 10 minutes, and lasted for about 16 minutes after which he had to puff again. This allowed him to walk about in the room without feeling pain.

The patient had not smoked *cannabis* for 3 days before the testing of the devices. He explained that it was a relief not to feel influenced by the *cannabis*, as the devices number 2 and 3 gave the pain relief without affecting him otherwise (no psychoactive effects).

EMBODIMENTS

1. A composition comprising cannabidiol or a variant or a derivative thereof, for delivery as anyone of in independent embodiments: a gas, or a vapor or a mist or an aerosol, for inhalation into the lungs, for use as a pharmaceutical, wherein the gas, or a vapor or a mist or an aerosol is not made by heating.
2. A composition according to embodiment 1, wherein the gas, or vapor or mist or aerosol is not made by heating above any one of 60, 70, 80, or 90 degrees celcius.
3. A composition according to embodiment 1, wherein the gas, or vapor or mist or aerosol is not made by heating above any one of 140° C., such as above 150° C., such as above 160° C., such as above 170° C. or above 180° C.
4. A composition according to any one of embodiments 1 to 3, wherein the composition is delivered by use of a passive inhalator.
5. A composition according to anyone of embodiments 1 to 4, wherein the composition is for delivery as a gas or a vapor.
6. A composition according to any one of embodiments 1 to 5, wherein the composition comprises cannabidiol or a variant or a derivative thereof in a dosage within a range selected from the ranges of from 0.1 mg to 50 mg, such as from 0.1 mg to 40 mg, such as from 0.1 mg to 30 mg, such as from 0.1 mg to 20 mg, such as from 0.1 mg to 15 mg, such as from 0.1 to 10 mg, such as from 0.5 mg to 10 mg, such as from 1 mg to 10 mg.
7. A composition according to any one of embodiments 1 to 6, wherein the composition is delivered by use of a passive inhalator, and wherein the gas, or a vapor or a mist or an aerosol which is inhaled delivers from 1 to 25%, such as from 1 to 20%, such as from 1 to 15%, such as from 5 to 15% of the dose present in the inhalator when used continuously over a period of 1 to 6 hours, such as from 2 to 6 hours, such as from 1 to 4 hours such as from 1 to 3 hours.
8. A composition according to any one of embodiments 1 to 7, wherein the composition further comprises a carrier, such as in non limiting example a peppermint oil, or in another non limiting example a vegetable oil with a flavour
9. A composition according to any one of embodiments 1 to 8, wherein the content of cannabidiol or a variant or a derivative thereof by weight percent to total weight of the composition is within the range of from 0.01% to 30% cannabidiol or a variant or a derivative thereof.
10. A composition according to any one of embodiments 1 to 9, wherein the composition further comprises THC, such as delta-9-THC or such as delta-8-THC or both.
11. A composition according to embodiment 10, wherein the composition comprises THC:CBD in a 1:1 w/w ratio, such as in a 1:2 ratio, such as in a 1:3 ratio, such as in a 1:4 ratio, such as in a 1:5 ratio, such as in a 1:6 ratio, such as in a 1:7 ratio, such as in a 1:8 ratio, such as in a 1:9 ratio, such as in a 1:10 ratio.

12. A composition according to any one of embodiments 1 to 11, wherein the composition further comprises one or more of a terpene or terpenoid.

13. A composition according to embodiment 12, wherein the terpenoid is one or more selected from the list of total terpene extract from *Cannabis sativa*, 1.8-cineole, d-limonene, β-myrcene, myrcenol, nerol, α-pinene, linalool, (3-caryophyllene, indomethacin, caryophyllene oxide, nerolidol, peppermint oil, 1-menthol, menthone, neomenthol, thymohydroquinone, thymol, thymoquinone, phytol, borneol, camphor, citral, geramol, farnesol and delta3Carene.

14. A composition according to embodiment 12, wherein the terpenoid is one or more selected from the list of total terpene extract from *Cannabis sativa*, 1.8-cineole, d-limonene, β-myrcene, α-pinene, linalool, β-caryophyllene, caryophyllene oxide, nerolidol, phytol, borneol, citral, indomethacin and geramol.

15. A composition according to any one of embodiments 1 to 13, wherein the composition is made for treatment, prevention or alleviation of a lung disease with an inflammatory element.

16. A composition according to any one of embodiments 1 to 15, wherein the composition is made for treatment, prevention or alleviation of lung inflammation.

17. A composition according to any one of embodiments 1 to 16, wherein the composition is made for prophylaxis, treatment, prevention or alleviation of a lung disease such as any one of acute lung injury, Chronic Obstructive Pulmonary Disorder, such as any one of chronic bronchitis, emphysema and chronic obstructive airways disease.

18. A composition according to any one of embodiments 1 to 17, wherein the composition is made for treatment, prevention or alleviation of a symptom of an inflammatory lung disease.

19. A composition according to any one of embodiments 1 to 18, wherein the composition is made for treatment, prevention or alleviation of lung inflammation caused by any one of smoking, passive smoking, fumes, air pollution, dust and chemicals including grains, isocyanates, cadmium and coal dust.

20. A composition according to any one of embodiments 1 to 19, wherein the composition is made for treatment, prevention or alleviation of lung inflammation by improving any one of the symptoms of breathlessness, persistent cough with phlegm, frequent chest infections, or wheezing.

21. A composition according to any one of embodiments 1 to 12 and 14, wherein the composition is made for treatment, prevention or alleviation of lung cancer.

22. A composition according to embodiment 21, wherein the lung cancer is any one selected from the list of small cell lung cancer and nonsmall cell lung cancer.

23. A composition according to embodiments 21 or 22, wherein the lung cancer is nonsmall cell lung cancer of any one of types adenocarcinoma, squamous cell carcinoma or large cell carcinoma.

24. A composition according to anyone of embodiments 21 to 23, wherein the lung cancer is nonsmall cell lung cancer in any one of stages I, II, III or IV.

25. A composition according to embodiment 21 or 22, wherein the cancer is small cell lung cancer in the limited stage.

26. A composition according to any one of embodiments 21 to 25, wherein the composition is for use in combination with radiation therapy and/or chemotherapy.

27. A composition according to any one of embodiments 1 to 26, wherein the composition is made for use in combination with existing treatment for the conditions.

28. A passive inhaler comprising the composition according to any one of embodiments 1 to 27.

29. A method of prophylaxis, treatment, prevention or alleviation of any one of the symptoms or diseases or conditions of any one of embodiments 15 to 28, using any one of the methods and compositions of any one of embodiments 1 to 14.

30. In one embodiment, methods and compositions of any one of embodiments 1 to 29, are for use in combination with administration of CBD by other means than inhalation, such other means may in non limiting example be oral or rectal administration or injected or by slow release deposits.

31. In one embodiment, the methods and compositions according to the any one of the previous embodiments, are for use in a method where the patient at least one time per day for 1-6 hours administers the compositions via a passive inhaler, by continued inhaling of air pulled through the device, so that for each breath of air taken into the lungs, air from a puff is dragged into the lungs with the inhaled air.

32. In one embodiment, the compositions of the present invention comprises one or more of CBD or THC or a terpene or a derivative or variant of any of those as the active ingredient.

33. In one embodiment, the compositions of the present invention comprises THC and CBD or a derivative or variant of any one of those as the active ingredients.

34. In one embodiment, the compositions of the present invention and according to the previous embodiments comprises THC or a derivative or a variant thereof and a terpene as the active ingredients.

35. In one embodiment, the compositions of the present invention, comprises CBD or a derivative or a variant thereof and a terpene as the active ingredients 36. In one embodiment, the compositions of the present invention, comprises CBD and THC or derivatives or variants thereof, and a terpene or a terpene mix as the active ingredients.

37. In one embodiment according to anyone of the previous embodiments, CBD or THC or terpenes may be a raw extract of *Cannabis sativa*.

38. In one embodiment according to embodiment 37, terpenes may be a total terpene distillate from *Cannabis sativa*.

39. In one embodiment according to any one of the previous embodiments, CBD or THC or terpenes may be isolated from *Cannabis sativa*, and may comprise trace amounts of other compounds, such that a CBD isolate may comprise trace amounts of THC and/or terpenes.

40. An improved inhaler (1) comprising a housing with at least a first compartment (30) and a second compartment (40), and including one or more substances, said second compartment (40) including at least one air entry port (50), said inhaler (1) having a first end (21) proximal to said first compartment (30) and a second end) proximal to said second compartment (40), an inhalation part 2 (27) being at said second end (22) and said second compartment (40) being for storing at least one substance and including in an inoperative state of said inhalator (1) 2.3 or more sealing bodies, if having, in sets of 3 sealing bodies, one in the center (65) as the largest and the other 2 sealing bodies (66a&b) smaller than the one in center (65), to provide the substances pass around the small sealing bodies while moved by the plounger (F) under pressure; to achieve separation of the substances after moving these from second compartment to first compartment, having the substances absorbed in the new invented filter (A) behind the last sealing body, and the other substances in the separated inner center pressed into the first compartment (30) for this substance to be absorbed in the other new invented filter (D). Arranged in a neighboring relationship (60), while sealed in the second compartment (40), each pair of neighboring bodies defining at least in part a sealed chamber (62) for containing a substance, said bodies (60) being movable together with said at least one substance from said second compartment (40) into said first compartment (30) to define an operative state of said inhalator (1) wherein said one or more substances are contained in said first compartment (30), whereby air entering through said air entry port (50) (F) and taking up, such as by evaporation, said at least one substance when contained in said first compartment (30) may be inhaled through said inhalation part 2 (27), characterized in a release device in said second compartment (40), said release device being for moving said bodies (60) into said first compartment and allowing said air to flow to said air entry port (50) in said operative state or to said air entry inhalation part 1 (27) at first end (21) characterized in that the inhalator further comprises one or more of a filter (A) is present between the one ball (66a) and the pin/plounger (F) shaped release device, where the pin/plounger (F) can be a filter it selves, made by polyurethane plast (PUR), and/or between any one of the balls (60), and/or a filter (D) is present in the inhalation part of the device (21) first end inhalation part 1. (27) to controle airflow and flowdrop, depending at the length and porosity of this filter (D) and to obtain API for enlarging the surface to vaporize more effectively and to avoid particles passing through the starhole in the acetate star hole filter (G) placed near to (21) first end, where the users lips while puffing and as accessory a mouthpiece (E) to add to the improved inhaler with a stop barrier inside and a variety that provides a "nose-mouth" piece (E) solution as a new design to be added to the improved inhaler, with or without a cap tube (B) to install the improved inhaler (1) into, bringing the possibility, together or solely with the mouthpiece (E), of adding dosing technology like (C) (E) counter electronic systems or blinking or changing coloured light from green to red, when enough puffs are provided via the improved inhaler.

The invention claimed is:

1. A passive inhaler device comprising a pharmaceutical composition and a carrier, the pharmaceutical composition comprising one or more of:
    cannabidiol (CBD),
    tetrahydrocannabinol (THC),
    any one of Ibuprofen, Paracetamol, or an opioid, and
    caffeine or a terpene,
        wherein the passive inhaler device is for delivery of the pharmaceutical composition and the carrier as a gas or a vapor,
        wherein the passive inhaler device has at least one air entry port coupled to a central air passage coupled to an inhalation port and the central air passage is configured to present sufficient exposure area of the pharmaceutical composition and the carrier for:
        (i) delivery of the pharmaceutical composition and the carrier as the gas or the vapor without heating and wherein the passive inhaler device does not include a heating device, wherein the gas or the vapor is generated only by the user sucking air through the passive inhaler device, or
        (ii) delivery of the pharmaceutical composition and the carrier as the gas or the vapor without heating above 80 degrees Celsius and wherein the passive inhaler device includes a heating device that heats air going through the central air passage to a temperature not exceeding 80 degrees Celsius, wherein the gas or the vapor is generated only by the heating device heating the air and the user sucking the heated air through the passive inhaler device.

2. The passive inhaler device of claim 1, wherein the carrier is selected from the group consisting of terpenes derived from *Cannabis*, total terpene extract from *Cannabis* plants, terpenes from coffee or cocoa, mint, *Eucalyptus* oil, Citrus oil, anise oil, propylene glycol, ethanol, water, oxygen, nitrogen, normal air, sodium chloride, peppermint oil, borneol, camphor, β-caryophyllene, caryophyllene oxide, 1,8-Cineole, citral, Delta3Carene, geraniol, indomethacin, limonene, linalool, linalyl acetate, β-myrcene, myrcenol, I-menthol, menthone, neomenthol, nerol, nerolidol, a-pinene, peppermint oil, Pulegone, phytol, Terpineol, Terpinen-4-ol, thymohydroquinone, thymol, and thymoquinone.

3. The passive inhaler device of claim 1, wherein the pharmaceutical composition comprises the cannabidiol in a dosage within a range of from 0.1 mg to 50 mg, from 0.1 mg to 40 mg, from 0.1 mg to 30 mg, from 0.1 mg to 20 mg, from 0.1 mg to 15 mg, from 0.1 to 10 mg, from 0.5 mg to 10 mg, or from 1 mg to 10 mg.

4. The passive inhaler device of claim 1, wherein the passive inhaler device delivers the pharmaceutical composition as a gas or a vapor which is inhaled, and wherein from 1% to 25%, from 1% to 20%, from 1% to 15%, or from 5% to 15% of a dose present in the passive inhaler device is delivered to the oral mucosa or to the lungs, when used continuously over a period from 1 to 6 hours, from 2 to 6 hours, from 1 to 4 hours, or from 1 to 3 hours.

5. The passive inhaler device of claim 1, wherein the pharmaceutical composition comprises THC and CBD in a ratio of 1:1 w/w, 1:2 wt/wt, 1:3 wt/wt, 1:4 wt/wt, 1:5 wt/wt, 1:6 wt/wt, 1:7 wt/wt, 1:8 wt/wt, 1:9 wt/wt, or 1:10 wt/wt, or CBD and THC in a ratio of 1:1 w/w, 1:2 w/w, 1:3 wt/wt, 1:4 wt/wt, 1:5 wt/wt, 1:6 wt/wt, 1:7 wt/wt, 1:8 wt/wt, 1:9 wt/wt, or 1:10 wt/wt.

6. The passive inhaler device of claim 1, wherein the
    passive inhaler device is made for the treatment, prevention, prophylaxis or alleviation of a disease, condition, or symptom selected from the group consisting of a lung disease with an inflammatory element, lung inflammation, lung disease, acute lung injury, Chronic Obstructive Pulmonary Disorder, chronic bronchitis, emphysema, chronic obstructive airways disease, an inflammatory lung disease, lung inflammation caused by smoking, lung inflammation caused by passive smoking, lung inflammation caused by fumes, lung inflammation caused by air pollution, lung inflammation caused by dust, lung inflammation caused by chemicals, lung inflammation caused by grains, lung inflammation caused by isocyanates, lung inflammation caused by cadmium and coal dust, breathlessness, persistent cough with phlegm, frequent chest infections, and wheezing.

7. The passive inhaler device of claim 1, wherein the passive inhaler device is made for the treatment, prevention, or alleviation of a cancer selected from the group consisting of a lung cancer, a cancer in the oral cavity, a head and neck cancer, and cancer in the CNS.

8. The passive inhaler device of claim 7, wherein the cancer is selected from the group consisting of nonsmall cell lung adenocarcinoma, nonsmall cell lung squamous cell carcinoma, large cell lung carcinoma, nonsmall cell lung cancer in stage I, nonsmall cell lung cancer in stage II, nonsmall cell lung cancer in stage III, nonsmall cell lung cancer in stage IV, small cell lung cancer in the limited stage, glioma cancer in the CNS, metastatic Lung cancer, metastatic breast cancer, metastatic genitourinary tract cancers, metastatic osteosarcoma, metastatic melanoma, metastatic head and neck cancer, metastatic neuroblastoma, metastatic gastrointestinal cancers, metastatic colorectal carcinoma, metastatic pancreatic carcinoma, and metastatic lymphoma.

9. The passive inhaler device of claim 1, wherein the passive inhaler device
is for use in the treatment, prevention, or alleviation of a condition selected from the group consisting of motion sickness, side effects of opioid analgesics, side effects of general anesthetics, side effects of chemotherapy, severe cases of gastroenteritis, severe cases of morning sickness, psychosis, anxiety, depression, schizophrenia, and epilepsy.

10. The passive inhaler device of claim 1, wherein the passive inhaler device is for use in treatment, prevention or alleviation of a pain selected from the group consisting of neuropathic pain, nociceptive pain, psychogenic pain, phantom limb pain, post herpetic neuralgia, and complex regional pain syndrome.

11. The passive inhaler device of claim 10, wherein the pain is caused by multiple sclerosis.

12. The passive inhaler device of claim 1, wherein the passive inhaler device is made for treatment, prevention, or alleviation of a neurodegenerative disease.

13. The passive inhaler device of claim 12, wherein the neurodegenerative disease is selected from the group consisting of a plaque-related disorder of the CNS, Parkinson's disease, Alzheimer's disease, transmissible spongiform encephalopathy, bovine spongiform encephalopathy, Huntington's disease, Familial amyloid polyneuropathy, Finnish amyloidosis, Lattice corneal dystrophy, cerebral amyloid angiopathy, and cerebral amyloid angiopathy Icelandic type.

14. The passive inhaler device of claim 1, wherein the passive inhaler device is made for increasing the transport of substances across the blood brain barrier.

15. The passive inhaler device of claim 1, wherein the THC in the composition comprises at least one THC variant selected from the group consisting of delta-9-THC and delta-8-THC.

16. The passive inhaler device of claim 6, wherein the lung disease is selected from the group consisting of acute lung injury, Chronic Obstructive Pulmonary Disorder (COPD), chronic bronchitis, emphysema, and chronic obstructive airways disease.

17. The passive inhaler device of claim 1, wherein the pharmaceutical composition comprises cannabidiol, the carrier comprises mint, and the passive inhaler device does not include the heating device.

18. The passive inhaler device of claim 1, wherein the pharmaceutical composition comprises cannabidiol, the carrier comprises mint, and the passive inhaler device includes the heating device that heats air going through the central air passage to a temperature not exceeding 80 degrees Celsius.

19. A passive inhaler device comprising a pharmaceutical composition and a carrier, wherein the pharmaceutical composition comprises one or more of:
cannabidiol,
tetrahydrocannabinol (THC),
any one of Ibuprofen, Paracetamol, or an opioid, and
caffeine or a terpene,
wherein the carrier comprises peppermint, the passive inhaler device is for delivery of the pharmaceutical composition and the carrier as a gas or a vapor,
wherein the passive inhaler device has at least one air entry port coupled to a central air passage coupled to an inhalation port and the central air passage is configured to present sufficient exposure area of the pharmaceutical composition and the carrier for delivery of the pharmaceutical composition and the carrier as the gas or the vapor without heating, and
wherein the gas or the vapor is generated only by the user sucking air through the passive inhaler device.

* * * * *